(12) United States Patent
Nakatani et al.

(10) Patent No.: US 8,741,659 B2
(45) Date of Patent: Jun. 3, 2014

(54) COMPOSITION FOR MEASURING THE BINDING AFFINITY BETWEEN NUCLEIC ACID AND TEST SUBSTANCE, AND USE THEREOF

(75) Inventors: Kazuhiko Nakatani, Osaka (JP); Jinhua Zhang, Lao ba cun (CN); Shiori Umemoto, Osaka (JP); Shinichi Sasaoka, Osaka (JP); Takahiro Wazaki, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/484,505

(22) Filed: May 31, 2012

(65) Prior Publication Data

US 2012/0238029 A1   Sep. 20, 2012

Related U.S. Application Data

(62) Division of application No. 12/452,878, filed as application No. PCT/JP2008/063705 on Jul. 30, 2008, now abandoned.

(30) Foreign Application Priority Data

Jul. 31, 2007   (JP) ................................ 2007-199970

(51) Int. Cl.
*G01N 21/76* (2006.01)

(52) U.S. Cl.
USPC ........................................................ 436/172

(58) Field of Classification Search
None
See application file for complete search history.

(56) References Cited

U.S. PATENT DOCUMENTS

| | | | |
|---|---|---|---|
| 5,047,519 A | 9/1991 | Hobbs, Jr. et al. | 536/23 |
| 5,151,507 A | 9/1992 | Hobbs, Jr. et al. | 536/23 |
| 5,188,934 A | 2/1993 | Menchen et al. | 435/6 |
| 5,242,796 A | 9/1993 | Prober et al. | 435/6 |
| 5,306,618 A | 4/1994 | Prober et al. | 435/6 |
| 5,332,666 A | 7/1994 | Prober et al. | 435/91.5 |
| 5,558,991 A | 9/1996 | Trainor | 435/6 |
| 5,608,063 A | 3/1997 | Hobbs, Jr. et al. | 544/244 |
| 5,625,081 A | 4/1997 | Trainor | 549/392 |
| 5,654,442 A | 8/1997 | Menchen et al. | 549/223 |
| 5,885,778 A | 3/1999 | Menchen et al. | 435/6 |
| 6,096,723 A | 8/2000 | Menchen et al. | 514/44 |
| 6,403,812 B1 | 6/2002 | Menchen et al. | 549/223 |
| 6,448,407 B1 | 9/2002 | Lee et al. | 546/283.1 |
| 6,699,661 B1 | 3/2004 | Kurane et al. | 435/6 |
| 2001/0000148 A1 | 4/2001 | Kurane et al. | 435/6 |
| 2001/0000175 A1 | 4/2001 | Kurane et al. | 514/44 |
| 2002/0081616 A1 | 6/2002 | Menchen et al. | 435/6 |
| 2003/0055243 A1 | 3/2003 | Lee et al. | 540/123 |
| 2003/0082592 A1 | 5/2003 | Kurane et al. | 435/6 |
| 2004/0063137 A1 | 4/2004 | Kurane et al. | 435/6 |
| 2004/0229235 A1 | 11/2004 | Lee et al. | 435/6 |
| 2005/0084870 A1 | 4/2005 | Menchen et al. | 435/6 |
| 2005/0171079 A1 | 8/2005 | Schrimpf et al. | 514/210.01 |
| 2005/0234031 A1 | 10/2005 | Schrimpf et al. | 514/183 |
| 2006/0063734 A1 | 3/2006 | Menchen et al. | 514/44 |
| 2006/0177856 A1 | 8/2006 | Kurane et al. | 435/6 |
| 2006/0188915 A1 | 8/2006 | Lee et al. | 435/6 |
| 2007/0254298 A1 | 11/2007 | Lee et al. | 435/6 |
| 2011/0263041 A1 | 10/2011 | Nakatani et al. | 436/501 |

FOREIGN PATENT DOCUMENTS

| | | |
|---|---|---|
| JP | 2568699 | 10/1996 |
| JP | 10-101591 | 4/1998 |
| JP | 2002-241397 | 8/2002 |
| WO | WO 03/091689 | 11/2003 |

OTHER PUBLICATIONS

Nguyen et al. "Indicator-displacement assays" Coordination Chemistry Reviews 250 (2006) 3118-3127.*
Painter, G., et al. (1991) "Initial binding of 2'-deoxynucleoside 5'-triphosphates to human immunodeficiency virus type 1 reverse transcriptase" Journal of Biological Chemistry, vol. 266, No. 29, pp. 19362-19368.
IUPAC Name: 2,7-bis(aminoethoxy)xanthen-9-one, [online], NCBI PubChem, CID:11659655, Create Date: Oct. 27, 2006, [searched on Jul. 13, 2007] Internet http://pubchem.ncbi.nlm.nih.gov/summary/summary.cgi?cid=11659655.
Oh, K., et al. (2006) "Excimer-based peptide beacons: a convenient experimental approach for monitoring polypeptide-protein and polypeptide-oligonucleotide interactions" Journal of American Chemical Society, vol. 128, No. 43, pp. 14018-14019.
Luedtke, N., et al. (2003) "Fluorescence-based methods for evaluating the RNA affinity and specificity of HIV-1 rev-RRE inhibitors" Biopolymers, vol. 70, Issue 1, pp. 103-119.
Nihon, K. (2003) "Inhibition of the HIV-1 Rev-RRE Complex formation . . . " The 83$^{rd}$ Annual Meeting of The Chemical Society of Japan, Mar. 3, 2003, p. 1102, 1G8-37.
Pace, T., et al. (2006) "Photophysics of aminoxanthone derivatives and their application as binding probes for DNA" Photochemistry and Photobiology, vol. 82, No. 1, pp. 78-87.
Zhang J., et al. (2010) "Fluorescent indicator displacement assay for ligand-RNA interactions" Journal of the American Chemical Society, vol. 132, No. 11, pp. 3660-3661.
European Search Report for corresponding European Patent Application No. 08791936.1 with mailing date of Aug. 2, 2010.
English Translation of Japanese Office Action for corresponding Japanese Patent Application No. 2009-519347 with mailing date of Jan. 26, 2010.
European Search Report for corresponding European Patent Application No. 11008097.5 with mailing date of Jul. 4, 2012.
Sriwilaijaroen, N., et al. (2004), "Cyquant cell proliferation assay as a fluorescence-based method for in vitro screening of antimalarial activity", *Southeast Asian Journal of Tropical medicine and Public Health*, 35(4): 840-844.
Spillane, C., et al. (2007), "DNA affinity binding studies using a flurorscent dye displacement technique: the dichotomy of the binding site", *Journal of Biological Inorganic Chemistry*, 12: 819-824.

* cited by examiner

*Primary Examiner* — James D Anderson
*Assistant Examiner* — William Lee
(74) *Attorney, Agent, or Firm* — Harness, Dickey & Pierce, P.L.C.

(57) ABSTRACT

In one embodiment of the present invention, a composition is disclosed for measuring a binding affinity between a nucleic acid and a test substance, which contains an organic fluorescent substance capable of binding to an RNA and which emits fluorescence having an intensity greater while the organic fluorescent substance is liberated from an RNA than while the organic fluorescent substance is bound to an RNA. This enables a highly accurate and easy measurement of a binding affinity between a test substance and a nucleic acid, and allows various substances to be examined as a test substance.

6 Claims, 26 Drawing Sheets

FIG. 7
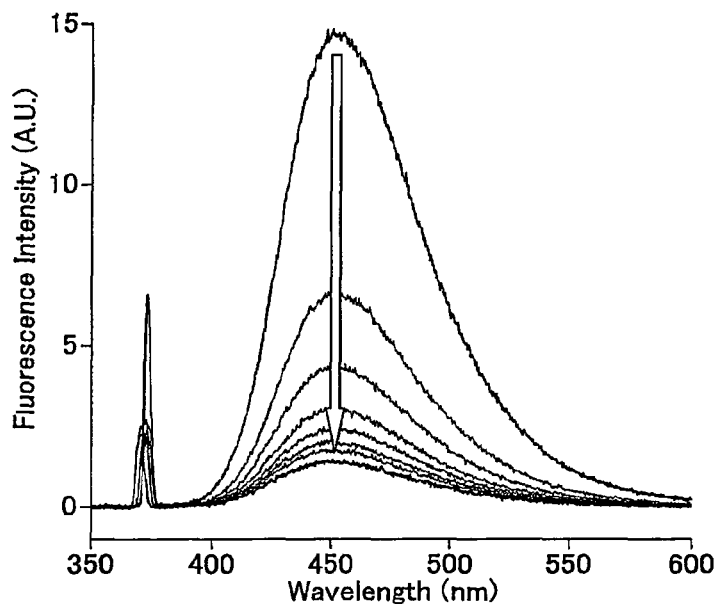
FIG. 8
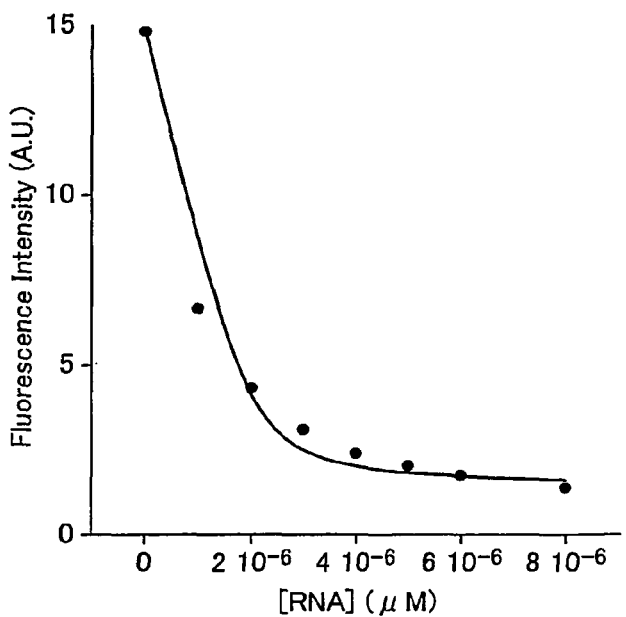
FIG. 9
Rev : Ac-TRQARRNRRRRWRERQRAAAAR-am

FIG. 10
human thrombin : H-TWTANVGKGQPS-OH
FIG. 11
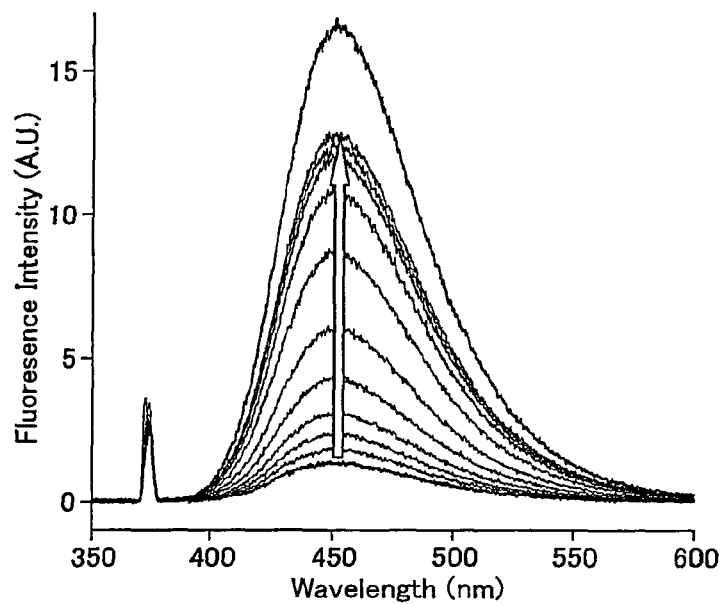
FIG. 12
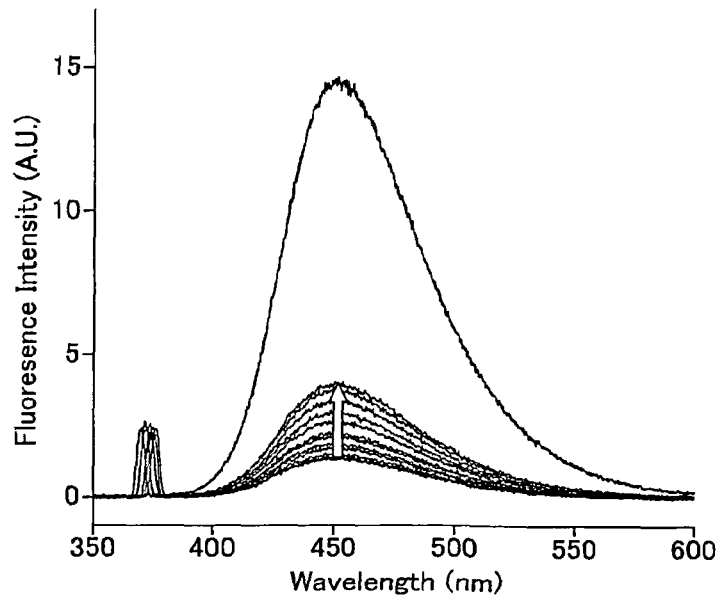

COMPOSITION FOR MEASURING THE BINDING AFFINITY BETWEEN NUCLEIC ACID AND TEST SUBSTANCE, AND USE THEREOF

REFERENCE TO A SEQUENCE LISTING

This application contains references to amino acid sequences and/or nucleic acid sequences which have been submitted concurrently herewith as the sequence listing text file "1837770_1.txt", file size 2.16 KiloBytes (KB), created on 10 Jul. 2013. The aforementioned sequence listing is hereby incorporated by reference in its entirety pursuant to 37 C.F.R. §1.52(e)(5).

TECHNICAL FIELD

The present invention relates to: a composition for measuring a binding affinity between a nucleic acid and a test substance; and the use thereof. More specifically, the present invention relates to: a composition for measuring, by means of a displacement assay, a binding affinity between a nucleic acid and a test substance (i.e., a substance to be examined); a kit for measuring a binding affinity between a nucleic acid and a test substance; and a method for measuring a binding affinity between a nucleic acid and a test substance with use of said composition.

BACKGROUND ART

In recent years, in-vivo functions of nucleic acids are much interested. Particularly, there are many cases where an RNA controls expression of a gene. In view of this, there is a prospect that development of drugs targeting RNAs will be sped up.

Generally, development of a drug starts from first screening. In the first screening, a library of candidate substances, which are candidates for the drug, is screened so that a substance bindable to a substance targeted by the drug is specified. Here, how quickly the first screening is performed is important, because this determines the development speed of the drug. For example, in a case where a target of a drug is an RNA, such a method is required that easily and quickly examines a binding affinity between the RNA and candidate substances so that a screening is quickly performed to specify a candidate substance bindable to the RNA.

Conventionally used method for examining a binding affinity between a nucleic acid such as an RNA and a candidate substance is as follows: The nucleic acid is immobilized to a detecting device such as a bead, or is caused to bind to a fluorescent dye, and then a signal changing due to an interaction therebetween is detected. For example, Non-Patent Literature 1 discloses a displacement assay by which a binding affinity between Rev protein and RRE (Rev Protein Responsible Element) in mRNA of an AIDS virus HIV-1 is measured based on whether or not Rev protein substitutes ethidium bromide which has bound to RRE. Ethidium bromide binding to a double strand nucleic acid emits fluorescence in response to irradiation of excitation light thereon. If Rev protein binds to RRE in place of ethidium bromide which has bound to RRE, ethidium bromide is liberated from RRE. This reduces fluorescence detected. Based on this reduction in fluorescence, the binding affinity between RRE and Rev protein is measured. A substance bindable to RRE is disclosed also in Non-Patent Literature 2.

As to binding between DNAs, Patent Literatures 1 to 3 disclose methods in which a DNA labeled with a xanthone fluorescent dye is used as a primer and is annealed to a target DNA fragment. Details of xanthone are disclosed in Patent Literatures 4 to 6 and Non-Patent Literature 3.

Patent Literature 1
Japanese Unexamined Patent Publication, Tokukaihei, No. 9-124636 A (Publication Date: May 13, 1997)
Patent Literature 2
Japanese Unexamined Patent Publication, Tokukai, No. 2004-225049 A (Publication Date: Aug. 12, 2004)
Patent Literature 3
Japanese Unexamined Patent Application Publication (Translation of PCT Application), Tokuhyo, No. 2004-532805 A (Publication Date: Oct. 28, 2004)
Patent Literature 4
Japanese Unexamined Patent Publication, Tokukaihei, No. 10-101591 A (Publication Date: Apr. 21, 1998)
Patent Literature 5
Specification of U.S. Patent Application Publication No. 2005/0171079 (Publication Date: Aug. 4, 2005)
Patent Literature 6
Specification of U.S. Patent Application Publication No. 2005/0234031 (Publication Date: Oct. 20, 2005)
Non-Patent Literature 1
Nathan W. Luedtke, Yitzhak Tor, Fluorescence-based methods for evaluating the RNA affinity and specificity of HIV-1 Rev-RRE inhibitors, Biopolymers, Vol. 70, Issue 1, p. 103-119.
Non-Patent Literature 2
*Nihon Kagaku Kai, Dai* 83 *Kai, Shunki Taikai, Koen Yokoshu* (Abstracts, The 83rd Annual Meeting of The Chemical Society of Japan), Mar. 3, 2003, page 1102, 1G8-37
Non-Patent Literature 3
IUPAC Name: 2,7-bis(2-aminoethoxy)xanthen-9-one, [online], NCBI PubChem, CID: 11659655, Create Date: 2006-10-27, [Searched on Jul. 13, 2007] The Internet <URL: http://pubchem.ncbi.nlm.nih.gov/summary/summary.cgi?cid=11659655>

SUMMARY OF INVENTION

The above conventional techniques, however, have the problems of (i) not capable of highly accurate and easy measurement of a binding affinity between a nucleic acid and a test substance and (ii) being limited in terms of the variety of examinable substances as a test substance.

The method using ethidium bromide disclosed in Non-Patent Literature 1 requires the measurement of reduction in fluorescence. Thus, this method is likely to be affected by fluorescence from background. For example, in a case where a small amount of test substance substitutes ethidium bromide and binds to nucleic acids, fluorescence is emitted from all of the remaining ethidium bromide which is not substituted with the test substance. While fluorescence is emitted from the background in this way, it is difficult to measure a minute reduction in a fluorescence intensity. In order to improve a measurement accuracy, an advanced device is required. Thus, this method cannot be easily performed. In addition, since ethidium bromide is highly carcinogenic, this method should be performed carefully. For this reason also, this method cannot be easily performed.

The techniques disclosed in Patent Literatures 1 to 3 can only detect annealing between DNAs, and cannot measure a binding affinity between a nucleic acid and a non-DNA substance, for example, a low-molecular compound, which is often used as a drug. Further, with these techniques, the detection of annealing between DNAs needs labeling one of the DNAs with a fluorescent dye. Thus, these techniques require troublesome procedures.

Patent Literatures 4 to 6 and Non-Patent Literatures 2 and 3 do not relate to a measurement of a binding affinity between a test substance and a nucleic acid, and do not disclose any technique contributing to solution of the foregoing problems.

The present invention was made in view of the foregoing problems, and an object of the present invention is to provide (i) a composition for measuring a binding affinity between a nucleic acid and a test substance and (ii) a technique using the composition, the composition and the technique enabling a highly accurate and easy measurement of the binding affinity between a test substance and a nucleic acid, and the composition and the technique making a variety of substances examinable as a test substance for the measurement.

In order to solve the foregoing problems, a composition of the present invention for measuring a binding affinity between a nucleic acid and a test substance includes: an organic fluorescent substance which is capable of binding to an RNA and which emits fluorescence having an intensity greater while the organic fluorescent substance is liberated from the RNA than while the organic fluorescent substance is bound to the RNA.

In order to solve the foregoing problems, a composition of the present invention for measuring a binding affinity between a nucleic acid and a test substance includes a compound represented by the following General Formula (1):

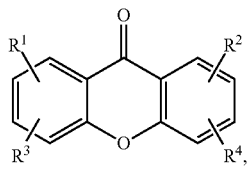
(1)

where each of $R^1$, $R^2$, $R^3$, and $R^4$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom.

In the composition of the present invention for measuring a binding affinity between a nucleic acid and a test substance, it is more preferable that the compound is a compound represented by the following General Formula (2):

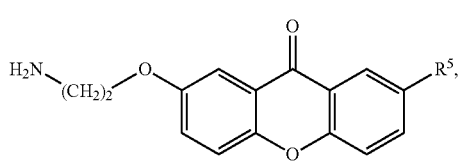
(2)

where $R^5$ is a hydrogen atom, a hydroxyl group, a halogen atom, or a C2 to C8 organic group which may contain one or more atoms selected from the group consisting of a hydrogen atom, a nitrogen atom, an oxygen atom, a sulfur atom, and a halogen atom.

In the composition of the present invention for measuring a binding affinity between a nucleic acid and a test substance, it is more preferable that the compound is a compound represented by the following Structural Formula (3):

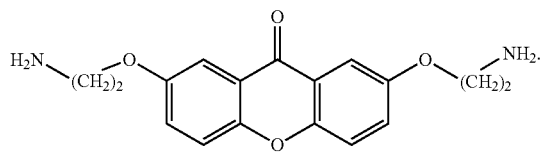
(3)

In the composition of the present invention for measuring a binding affinity between a nucleic acid and a test substance, it is more preferable that the compound is a compound represented by the following General Formula (12):

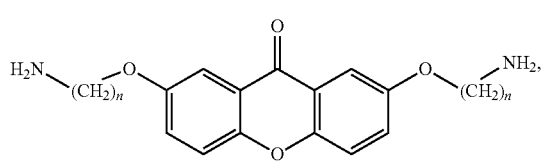
(12)

where n is 3, 4, or 5.

In the composition of the present invention for measuring a binding affinity between a nucleic acid and a test substance, it is more preferable that the compound is a compound represented by the following Structural Formula (13):

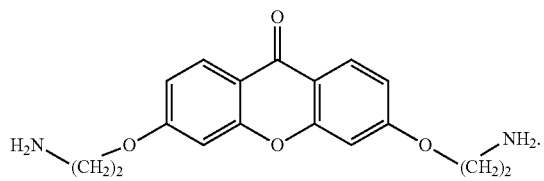
(13)

In the composition of the present invention for measuring a binding affinity between a nucleic acid and a test substance, it is more preferable that the compound is a compound represented by the following General Formula (14):

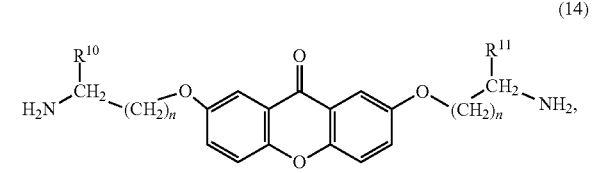
(14)

where n is 1 or 2; and each of $R^{10}$ and $R^{11}$ is independently an alkyl group or a carboxyl group.

In the composition of the present invention for measuring a binding affinity between a nucleic acid and a test substance, it is more preferable that the compound is a compound represented by the following General Formula (16):

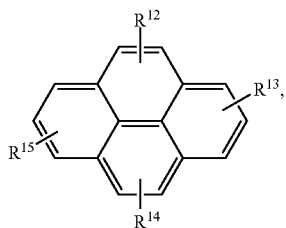

(16)

where each of $R^{12}$, $R^{13}$, $R^{14}$, and $R^{15}$ is independently a hydrogen atom, a hydroxyl group, or a C1 to C5 organic group which may contain one or more atoms selected from the group consisting of a hydrogen atom, a nitrogen atom, an oxygen atom, a sulfur atom, and a halogen atom.

In the composition of the present invention for measuring a binding affinity between a nucleic acid and a test substance, it is more preferable that the compound is a compound represented by the following General Formula (17):

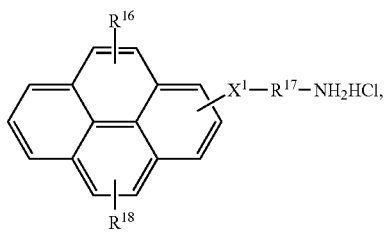

(17)

where each of $R^{16}$ and $R^{18}$ is independently a hydroxyl group or a C1 to C5 alkoxyl group which may be substituted with an oxygen atom and/or a nitrogen atom at one or more carbons; $X^1$ is an oxygen atom, a nitrogen atom, or a sulfur atom; $R^{17}$ is a C1 to C5 alkylene group, one or more hydrogen atoms of which may be substituted with one or more functional groups selected from the group consisting of a hydroxyl group, an amino group, and an alkyl group.

In the composition of the present invention for measuring a binding affinity between a nucleic acid and a test substance, it is more preferable that the compound is a compound represented by the following General Formula (18):

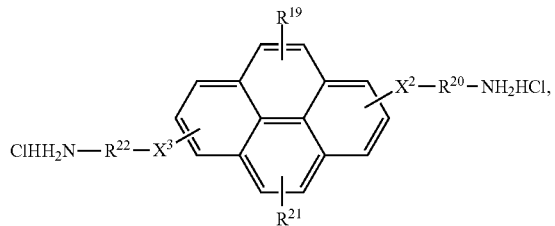

(18)

where each of $R^{19}$ and $R^{21}$ is independently a hydroxyl group or a C1 to C5 alkoxyl group which may be substituted with an oxygen atom and/or a nitrogen atom at one or more carbons; each of $X^2$ and $X^3$ is independently an oxygen atom, a nitrogen atom, or a sulfur atom; each of $R^{20}$ and $R^{22}$ is independently a C1 to C5 alkylene group, one or more hydrogen carbons of which may be substituted with one or more functional groups selected from the group consisting of a hydroxyl group, an amino group, and an alkyl group.

Further, a kit of the present invention for measuring a binding affinity between a nucleic acid and a test substance includes an organic fluorescent substance which is capable of binding to an RNA and which emits fluorescence having an intensity greater while the organic fluorescent substance is liberated from the RNA than while the organic fluorescent substance is bound to the RNA.

Furthermore, the kit of the present invention for measuring a binding affinity between a nucleic acid and a test substance more preferably includes: a compound represented by the following General Formula (1):

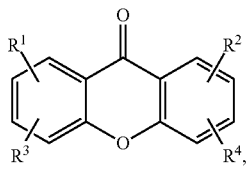

(1)

where each of $R^1$, $R^2$, $R^3$, and $R^4$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom; and/or a compound represented by the following General Formula (16):

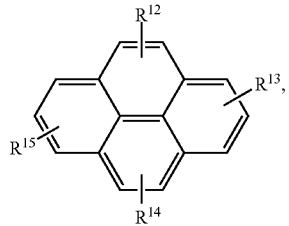

(16)

where each of $R^{12}$, $R^{13}$, $R^{14}$, and $R^{15}$ is independently a hydrogen atom, a hydroxyl group, or a C1 to C5 organic group which may contain one or more atoms selected from the group consisting of a hydrogen atom, a nitrogen atom, an oxygen atom, a sulfur atom, and a halogen atom.

Further, a method of the present invention is a method for measuring a binding affinity between a nucleic acid and a test substance, said method including: a first measuring step for measuring fluorescence emitted in response to irradiation of light onto a first solution obtained by mixing a nucleic acid with an organic fluorescent substance which is capable of binding to an RNA and which emits fluorescence having an intensity greater while the organic fluorescent substance is liberated from the RNA than while the organic fluorescent substance is bound to the RNA; a second measuring step for measuring fluorescence emitted in response to irradiation of light onto a second solution obtained by further mixing the first solution with a test substance; and a comparing step for comparing (i) the fluorescence measured in the first measuring step with (ii) the fluorescence measured in the second measuring step.

Furthermore, in the method of the present invention for measuring a binding affinity between a nucleic acid and a test substance, it is preferable that: the first measuring step measures the fluorescence emitted in response to irradiation of light onto the first solution obtained by mixing a nucleic acid with a compound represented by the following General Formula (1):

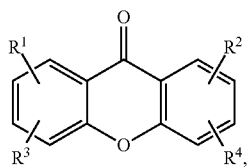
(1)

where each of $R^1$, $R^2$, $R^3$, and $R^4$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom; and/or a compound represented by the following General Formula (16):

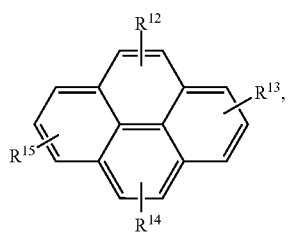
(16)

where each of $R^{12}$, $R^{13}$, $R^{14}$, and $R^{15}$ is independently a hydrogen atom, a hydroxyl group, or a C1 to C5 organic group which may contain one or more atoms selected from the group consisting of a hydrogen atom, a nitrogen atom, an oxygen atom, a sulfur atom, and a halogen atom; the second measuring step measures the fluorescence emitted in response to irradiation of light onto the second solution obtained by further mixing the first solution with a test substance; and the comparing step compares (i) the fluorescence measured in the first measuring step with (ii) the fluorescence measured in the second measuring step.

For a fuller understanding of the nature and advantages of the invention, reference should be made to the ensuing detailed description taken in conjunction with the accompanying drawings.

BRIEF DESCRIPTION OF DRAWINGS

FIG. 7
FIG. 7 is a view illustrating a result of evaluation of binding between X2S and RRE.

FIG. 8
FIG. 8 is a view plotting the fluorescence intensities at a measurement wavelength of 453 nm shown in the result illustrated in FIG. 7.

FIG. 9
FIG. 9 is a view schematically illustrating the structure of Rev protein used in Examples of the present invention.

FIG. 10
FIG. 10 is a view schematically illustrating the structure of thrombin used in Examples of the present invention.

FIG. 1
FIG. 11 is a view illustrating a result of a measurement of a binding affinity between Rev protein and RRE.

FIG. 12
FIG. 12 is a view illustrating a result of a measurement of a binding affinity between neomycin and RRE.

FIG. 23 is a view illustrating a relationship between an excitation spectrum and a fluorescence spectrum, which relationship was observed when X2S(2-Me) was irradiated with light having an excitation wavelength of 370 nm.

FIG. 24 is a view illustrating a relationship between an excitation spectrum and a fluorescence spectrum, which relationship was observed when 3,6-X2S(2) was irradiated with light having an excitation wavelength of 322 nm.

FIG. 25 is a view illustrating a relationship between a concentration of an RNA and a fluorescence intensity of X2S, which relationship was observed when X2S was irradiated with light having an excitation wavelength of 370 nm.

FIG. 26 is a view illustrating a relationship between a concentration of an RNA and a fluorescence intensity of X2S(3), which relationship was observed when X2S(3) was irradiated with light having an excitation wavelength of 372 nm.

FIG. 27 is a view illustrating a relationship between a concentration of an RNA and a fluorescence intensity of X2S(4), which relationship was observed when X2S(4) was irradiated with light having an excitation wavelength of 375 nm.

FIG. 28 is a view illustrating a relationship between a concentration of an RNA and a fluorescence intensity of X2S(5), which relationship was observed when X2S(5) was irradiated with light having an excitation wavelength of 376 nm.

FIG. 29 is a view illustrating a relationship between a concentration of an RNA and a fluorescence intensity of X2S(2-Me), which relationship was observed when X2S(2-Me) was irradiated with light having an excitation wavelength of 370 nm.

FIG. 30 is a view illustrating a relationship between a concentration of an RNA and a fluorescence intensity of 3,6-X2S(2), which relationship was observed when 3,6-X2S(2) was irradiated with light having an excitation wavelength of 322 nm.

FIG. 31 is a graph illustrating a relationship between a concentration of a double strand RNA added and a fluorescence intensity of each compound.

FIG. 32 is a view plotting residual fluorescence intensities (%) which were obtained on the assumption that fluorescence intensities of respective fluorescence peaks observed at a concentration of 0.0 μM of a double strand RNA were 100%.

FIG. 33 is a view illustrating a relationship between a concentration of RRE and a fluorescence intensity of X2S, which relationship was observed when X2S was irradiated with light having an excitation wavelength of 370 nm.

FIG. 34 is a view illustrating a relationship between a concentration of RRE and a fluorescence intensity of X2S(3), which relationship was observed when X2S(3) was irradiated with light having an excitation wavelength of 372 nm.

FIG. 35 is a view illustrating a relationship between a concentration of RRE and a fluorescence intensity of X2S(4), which relationship was observed when X2S(4) was irradiated with light having an excitation wavelength of 375 nm.

FIG. 36 is a view illustrating a relationship between a concentration of RRE and a fluorescence intensity of X2S(5), which relationship was observed when X2S(5) was irradiated with light having an excitation wavelength of 376 nm.

FIG. 37 is a view illustrating a relationship between a concentration of RRE and a fluorescence intensity of X2S(2-Me), which relationship was observed when X2S(2-Me) was irradiated with light having an excitation wavelength of 370 nm.

FIG. 38 is a view illustrating a relationship between a concentration of RRE and a fluorescence intensity of 3,6-X2S(2), which relationship was observed when 3,6-X2S(2) was irradiated with light having an excitation wavelength of 322 nm.

FIG. 39 is a graph illustrating a relationship between a concentration of RRE added and a fluorescence intensity of each compound.

FIG. 40 is a view plotting residual fluorescence intensities (%) which were obtained on the assumption that fluorescence intensities of respective fluorescence peaks observed at a concentration of 0.0 μM of RRE were 100%.

FIG. 41 is a view plotting values obtained by dividing (i) residual fluorescence intensities (%) obtained in the case involving use of a double strand RNA by (ii) residual fluorescence intensities (%) obtained in the case involving use of RRE.

FIG. 42 is a view plotting values obtained by subtracting (i) residual fluorescence intensities (%) obtained in the case involving use of RRE from (ii) residual fluorescence intensities (%) obtained in the case involving use of a double strand RNA.

FIG. 43 is a view illustrating a result of a measurement of a binding affinity between Rev protein and RRE, which measurement was performed using X2S.

FIG. 44 is a view illustrating a result of a measurement of a binding affinity between Rev protein and RRE, which measurement was performed using X2S(3).

FIG. 45 is a view illustrating a result of a measurement of a binding affinity between Rev protein and RRE, which measurement was performed using X2S(4).

FIG. 46 is a view illustrating a result of a measurement of a binding affinity between Rev protein and RRE, which measurement was performed using X2S(5).

FIG. 47 is a view illustrating a result of a measurement of a binding affinity between Rev protein and RRE, which measurement was performed using X2S(2-Me).

FIG. 48 is a view illustrating a result of a measurement of a binding affinity between Rev protein and RRE, which measurement was performed using 3,6-X2S(2).

FIG. 49 is a view illustrating a relationship between an amount of Rev added and a fluorescence intensity, in connection with X2S, X2S(3), X2S(4), X2S(5), X2S(2-Me), and 3,6-X2S(2).

FIG. 50 is a graph illustrating a relationship between an amount of Rev added and a recovery rate of a fluorescence intensity, in connection with X2S, X2S(3), X2S(4), X2S(5), X2S(2-Me), and 3,6-X2S(2).

FIG. 51 is a view illustrating a relationship between an excitation spectrum and a fluorescence spectrum, in connection with 1-Pyrenemethanamide, hydrochloride.

FIG. 52 is a view illustrating a result of evaluation of binding between 1-Pyrenemethanamide, hydrochloride and a double strand RNA.

FIG. 53 is a view illustrating a result of evaluation of binding between 1-Pyrenemethanamide, hydrochloride and RRE.

FIG. 54 is a view plotting residual fluorescence intensities (%) of 1-Pyrenemethanamide obtained from the fluorescence intensities detected at a fluorescence wavelength of 375 nm and at the different RNA concentrations.

FIG. 55 is a view illustrating a result of a measurement of a binding affinity between Rev protein and RRE, which measurement was performed using 1-Pyrenemethanamide.

FIG. 56 is a graph illustrating a relationship between an amount of Rev added and a recovery rate of a fluorescence intensity, in connection with 1-Pyrenemethanamide.

DESCRIPTION OF EMBODIMENTS

Figure 1:
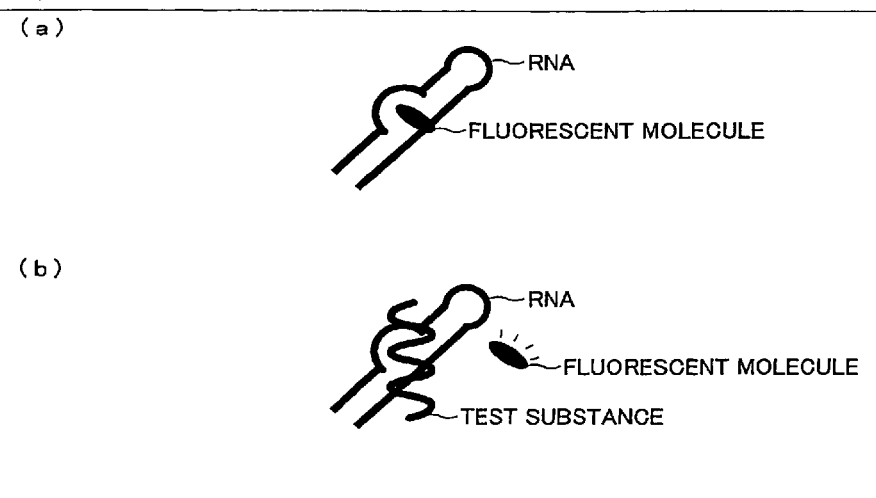
FIG. 1
FIG. 1 is a view schematically illustrating a principle of a method of the present invention. (a) of FIG. 1 schematically shows the first solution, and (b) of FIG. 1 schematically shows the second solution.

The inventors of the present invention made a diligent study on how to highly accurately and easily measure a binding affinity between a test substance and a nucleic acid. As a result, the inventors found the following fact: An organic fluorescent substance which is capable of binding to an RNA and which emits fluorescence with an intensity greater while the organic fluorescent substance is liberated from the RNA than while the organic fluorescent substance is bound to the RNA, for example, a compound represented by General Formula (1) or a compound represented by General Formula (16) is a fluorescent substance which is excited to emit fluorescence in response to irradiation of light thereon; however, causing the organic fluorescent substance to solely bind to a nucleic acid results in a phenomenon that the organic fluorescent substance emits no fluorescence, or fluorescence with weaker intensity, even when light is emitted thereon.

Generally, some of the compounds represented by the above General Formula (1) have been used for labeling e.g., DNA, as disclosed in Patent Literatures 1 to 3. Thus, said some of the compounds have been used as a labeling substance for causing fluorescence emission when a target substance binds to another target substance. Regardless of this, the inventors of the present invention conducted an attempt, which had never been considered and tried by anyone, to cause the above-described organic fluorescent substance e.g., a compound represented by the above General Formula (1) or a compound represented by the above General Formula (16) to solely be mixed with a nucleic acid to bind to the nucleic acid, instead of labeling a desired substance with the organic fluorescent substance. Consequently, the inventors found that this causes the above-described phenomena.

In addition, the inventors of the present invention found that performing a displacement assay using this organic fluorescent substance e.g., a compound represented by the above General Formula (1) or a compound represented by the above General Formula (16) provides the following effects: (i) Since an intensity of fluorescence detected increases as a test substance substitutes the compound and binds to a nucleic acid, it is possible to highly accurately perform the measurement without being affected by fluorescence from the background. (ii) Since such a displacement assay does not require labeling of a nucleic acid or a test substance and can be performed simply by mixing a nucleic acid with the compound and by further mixing the resultant with the test substance, the measurement can be performed in a significantly easy manner. Thus, the inventors of the present invention completed the present invention.

Labeling a nucleic acid and/or a test substance as in Patent Literatures 1 to 3 may cause a structural change in the nucleic acid and/or the test substance. The structural change in the nucleic acid and/or the test substance may give a result different from a result obtained with the nucleic acid and/or the substance not labeled. On the other hand, the present invention can avoid such a case, since the present invention does not cause a structural change in a nucleic acid or a test substance.

One embodiment of the present invention is described below.

<1. Composition for Measuring Binding Affinity Between Nucleic Acid and Test Substance>

A composition (hereinafter, referred to as "composition of the present invention") of the present invention for measuring a binding affinity between a nucleic acid and a test substance contains an organic fluorescent substance which is capable of binding to an RNA and which emits fluorescence having an intensity greater while the organic fluorescent substance is liberated from the RNA than while the organic fluorescent substance is bound to the RNA.

The above organic fluorescent substance is not particularly limited to a specific one. Examples of the organic fluorescent substance encompass a compound represented by General Formula (1) indicated below and a compound represented by General Formula (16) indicated below.

Each of these compounds not only can bind to an RNA, but also emits fluorescence in response to irradiation of light thereon, the fluorescence having an intensity greater while the compound is liberated from an RNA than while the compound is bound to an RNA. This prevents an effect of fluorescence of the background, unlike in a case where ethidium bromide is used. This in turn makes the above compounds suitable for a displacement assay, and thus contributes to a more efficient first screening of target substances for a drug.

The composition of the present invention preferably contains a compound represented by the following General Formula (1):

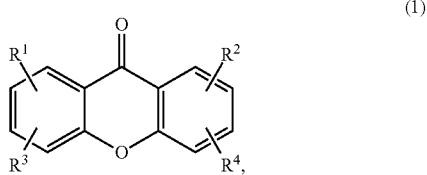

(1)

where each of $R^1$, $R^2$, $R^3$, and $R^4$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom.

The compound (hereinafter, also referred to as "xanthone fluorescent molecule") represented by the above General Formula (1) is not particularly limited to a specific one. Examples of the compound encompass the following: A compound represented by the following General Formula (4):

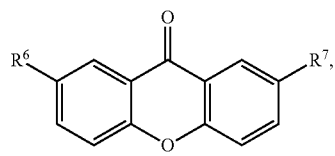
(4)

where each of $R^6$ and $R^7$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom;

A compound represented by the following Structural Formula (5):

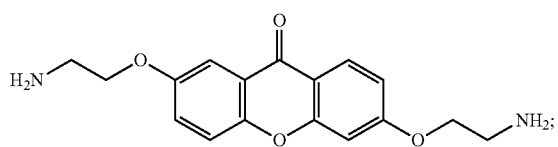
(5)

A compound represented by the following Structural Formula (6):

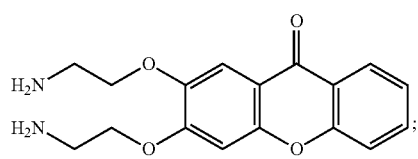
(6)

A compound represented by the following General Formula (7):

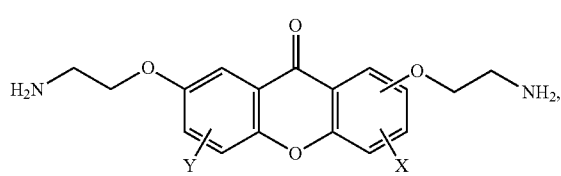
(7)

where each of X and Y is independently a hydrogen atom, a halogen atom, or an alkyl group, and the alkyl group is preferably in ortho position with respect to a 2-aminoethoxy group;

A compound represented by the following Structural Formula (8):

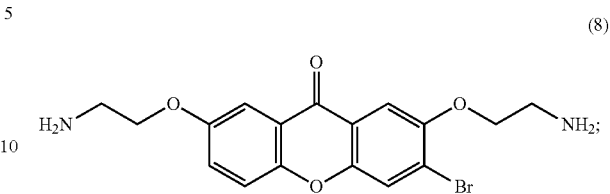
(8)

A compound represented by the following Structural Formula (9):

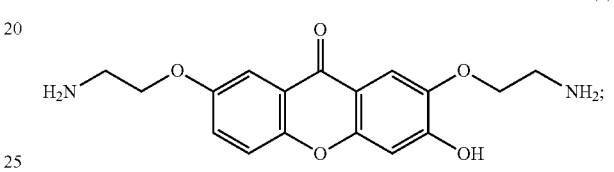
(9)

and

A compound represented by the following Structural Formula (13):

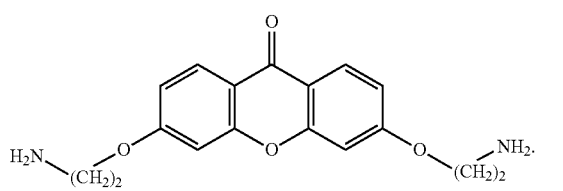
(13)

The compound represented by the above General Formula (4) is not particularly limited to a specific one. A preferable example of the compound is a compound represented by the following General Formula (10):

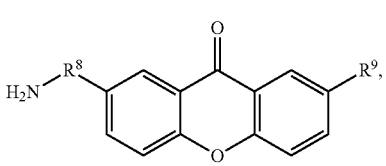
(10)

where each of $R^8$ and $R^9$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom. The compound represented by the above General Formula (10) is not particularly limited to a specific one. A preferable example of the compound is a compound represented by the following General Formula (2):

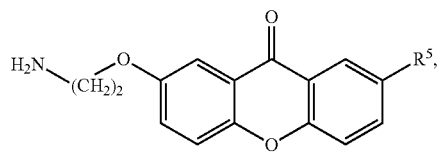
(2)

where $R^5$ is a hydrogen atom, a hydroxyl group, a halogen atom, or a C2 to C8 organic group which may contain one or more atoms selected from the group consisting of a hydrogen atom, a nitrogen atom, an oxygen atom, a sulfur atom, and a halogen atom. The compound represented by the above General Formula (2) is not particularly limited to a specific one. Examples of the compound encompass compounds represented by the following Structural Formula (3):

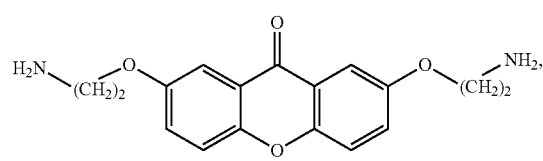
(3)

namely 2,7-bis(2-aminoethoxy)xanthen-9-one (hereinafter, referred to as "X2S"), 2-(2-aminoethoxy)xanthen-9-one (hereinafter, referred to as "X1S"), and a compound represented by the following Structural Formula (11):

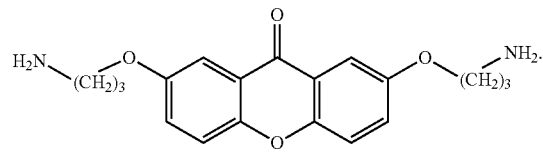
(11)

Among these example compounds, X2S is particularly preferable.

Other examples of the compound represented by General Formula (4) encompass: A compound represented by the following General Formula (12):

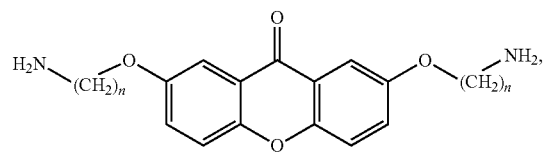
(12)

where n is 3, 4, or 5;

A compound represented by the following General Formula (14):

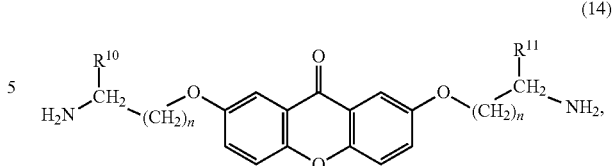
(14)

where n is 1 or 2, and each of $R^{10}$ and $R^{11}$ is independently an alkyl group or a carboxyl group; and A compound represented by the following Structural Formula (15):

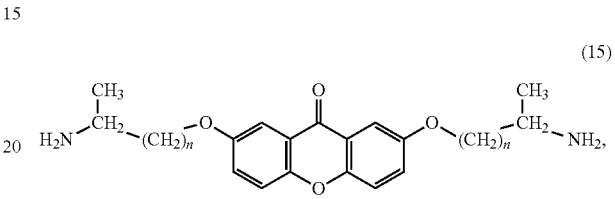
(15)

where n is 1 or 2.

The composition of the present invention may be a compound represented by the following General Formula (16):

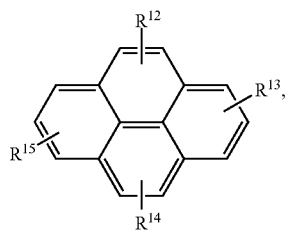
(16)

where each of $R^{12}$, $R^{13}$, $R^{14}$, and $R^{15}$ is independently a hydrogen atom, a hydroxyl group, or a C1 to C5 organic group which may contain one or more atoms selected from the group consisting of a hydrogen atom, a nitrogen atom, an oxygen atom, a sulfur atom, and a halogen atom.

The compound (hereinafter, referred to as "pyrene fluorescent molecule") represented by the above General Formula (16) is not particularly limited to a specific one. An example of the compound is a compound represented by the following General Formula (17):

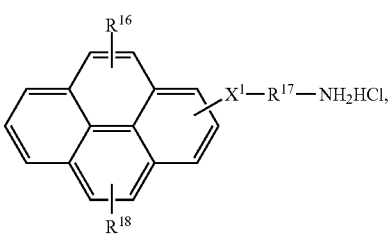
(17)

where each of $R^{16}$ and $R^{18}$ is independently a hydroxyl group or a C1 to C5 alkoxyl group which may be substituted with an oxygen atom and/or a nitrogen atom at one or more carbons; $X^1$ is an oxygen atom, a nitrogen atom, or a sulfur atom; $R^{17}$ is a C1 to C5 alkylene group, one or more hydrogen atoms of which may be substituted with one or more functional groups selected from the group consisting of a hydroxyl group, an amino group, and an alkyl group. Another example is a compound represented by the following General Formula (18):

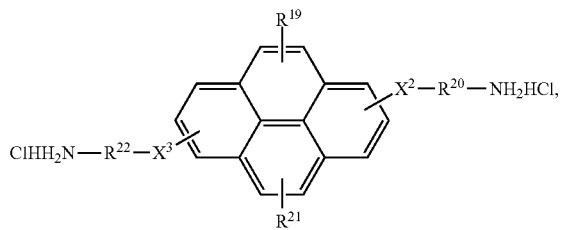

(18)

where each of $R^{19}$ and $R^{21}$ is independently a hydroxyl group or a C1 to C5 alkoxyl group which may be substituted with an oxygen atom and/or a nitrogen atom at one or more carbons; each of $X^2$ and $X^3$ is independently an oxygen atom, a nitrogen atom, or a sulfur atom; each of $R^{20}$ and $R^{22}$ is independently a C1 to C5 alkylene group, one or more hydrogen atoms of which may be substituted with one or more functional groups selected from the group consisting of a hydroxyl group, an amino group, and an alkyl group.

The compound represented by the above General Formula (17) is not particularly limited to a specific one. An example of the compound is a compound represented by the following Structural Formula (19):

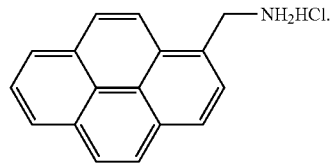

(19)

A xanthone fluorescent molecule emits fluorescence in response to irradiation of excitation light thereon. This fluorescence has an intensity that is decreased if the xanthone fluorescent molecule binds to a nucleic acid. Thus, use of a xanthone fluorescent molecule, a nucleic acid, and a test substance allows a displacement assay to be performed. Specifically, a binding affinity between the test substance and the nucleic acid is measurable based on whether or not the xanthone fluorescent molecule bound to the nucleic acid in advance can be substituted with the test substance. This also applies to a case involving use of, e.g., a pyrene fluorescent molecule, represented by Structural Formula (19), which also emits fluorescence in response to irradiation of excitation light thereon.

The displacement assay involving the use of a xanthone fluorescent molecule is unaffected by fluorescence of the background. This enables a highly accurate measurement of a binding affinity between a test substance and a nucleic acid. Specifically, a xanthone fluorescent molecule bound to a nucleic acid emits fluorescence that is undetected or barely detected at the most. When a test substance substitutes the xanthone fluorescent molecule to bind to the nucleic acid, the xanthone fluorescent molecule is liberated from the nucleic acid. This intensifies the fluorescence detected. This prevents the fluorescence of the background from affecting the measurement, and thus enables a highly accurate measurement of the binding affinity. This also applies to the case involving the use of, e.g., a pyrene fluorescent molecule, represented by Structural Formula (19), which also emits fluorescence in response to irradiation of excitation light thereon.

The xanthone fluorescent molecules mentioned above as examples may each be obtained by any method. Thus, the method is not particularly limited to a specific one. For example, a commercially available xanthone fluorescent molecule may be used. Alternatively, a commercially unavailable one may be synthesized from a material such as xanthone and 2,7-dihydroxyxanthone, by methods described in Szajnman, S. H.; Yan, W.; Bailey, B. N.; Docampo, R.; Elhalem, E.; Rodriguez, J. B. J. Med. Chem. 2000, 43, 1826-1840, and Pace, T. C. S.; Monahan, S. L.; MacRae, A. I.; Kaila, M.; Bohne, C. Photochem. Photobiol. 2006, 82, 78-87. The inventors of the present invention synthesized, e.g., X2S with reference to the above literature.

The pyrene fluorescent molecules mentioned above as examples may each be obtained by any method. Thus, the method is not particularly limited to a specific one. For example, a commercially available pyrene fluorescent molecule may be used. Alternatively, a commercially unavailable one may be synthesized, e.g., through the following synthetic pathway:

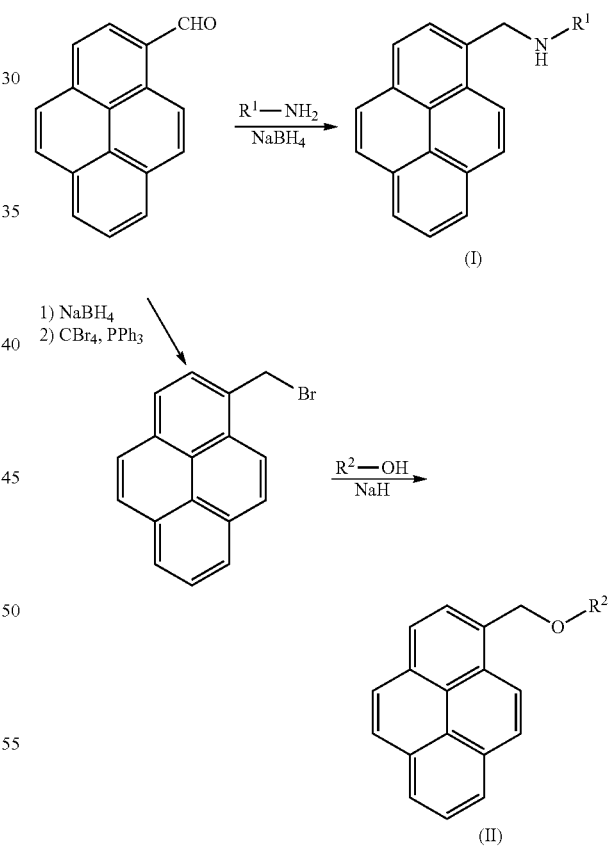

In the above synthetic pathway, each of $R^1$ and $R^2$ is independently a C1 to C18 alkyl group, a C1 to C18 alkenyl group, a C1 to C18 alkynyl group, an aryl group, a heteroaryl group, or an aralkyl group. One or more hydrogen atoms of each of the alkyl group, the alkenyl group, the alkynyl group, the aryl group, the heteroaryl group, and the aralkyl group may be substituted with one or more functional groups selected from the group consisting of an alkyl group, a haloalkyl group, an alkoxyl group, an aryloxy group, an alkylthio group, a siloxy group, a dialkylamino group, and a nitro group.

As indicated by the above synthetic pathway, a compound (I) may be synthesized by reacting pyrenealdehyde with a primary amine with use of $NaBH_4$ as a reducing agent. A compound (II) may be synthesized by reacting pyrenealdehyde with $NaBH_4$ and then with carbon tetrabromide and triphenylphosphine, and further reacting the product with an alcohol in the presence of sodium hydride.

To stably keep the organic fluorescent substance such as the xanthone fluorescent molecule and the pyrene fluorescent molecule, the composition of the present invention preferably contains such a compound as dissolved in a buffer solution. The buffer solution is not limited to a specific one, provided that it does not impair the function of the organic fluorescent substance such as the xanthone fluorescent molecule and the pyrene fluorescent molecule. Preferable examples of the buffer solution encompass a cacodylate buffer solution, a borate buffer solution, and an acetate buffer solution. Among these, a cacodylate buffer solution is particularly preferable because it is capable of holding the organic fluorescent substance such as the xanthone fluorescent molecule and the pyrene fluorescent molecule more stably than the others. The buffer solution preferably contains NaCl dissolved therein beforehand in an amount within a range from 50 mM to 200 mM. This is because increasing a salt concentration prevents nonspecific electrostatic binding.

The composition of the present invention may be used to measure a binding affinity, for a nucleic acid, of any test substance. Use of the composition of the present invention enables a measurement of a binding affinity of any substance as the test substance. Examples of the test substance encompass: low-molecular chemical substances; nucleic acids such as a DNA and an RNA; and high-molecular chemical substances such as peptides, proteins, sugars, and lipids. Candidates for drugs are normally low-molecular chemical substances. A binding affinity of such low-molecular chemical substances for a nucleic acid can be measured highly accurately and easily with the use of the composition of the present invention.

<2. Kit for Measuring Binding Affinity between Nucleic Acid and Test Substance>

A kit (hereinafter, referred to as "kit of the present invention") of the present invention for measuring a binding affinity between a nucleic acid and a test substance is simply required to include an organic fluorescent substance which is capable of binding to an RNA and which emits fluorescence having an intensity greater while the organic fluorescent substance is liberated from the RNA than while the organic fluorescent substance is bound to the RNA.

The kit of the present invention priferably includes a compound represented by the above General Formula (1) and/or a compound represented by the above General Formula (16). Further, the kit of the present invention preferably includes the above buffer solution.

The contents of the kit are not limited to the above. The kit may additionally include a reagent and/or an instrument. Thus, the kit may include, e.g., a microplate and/or a column for measuring fluorescence. The kit may also include a nucleic acid for use in the measurement.

The kit of the present invention may be provided in a single container containing (i) the xanthone fluorescent molecule and/or the pyrene fluorescent molecule, (ii) the buffer solution, and (iii) other reagents, in appropriate amounts and/or forms. Alternatively, the kit of the present invention may be provided in separate containers for the individual contents.

Further, the kit of the present invention may include a manual describing, e.g., a procedure for a below-described method of the present invention.

<3. Method for Measuring Binding Affinity Between Nucleic Acid and Test Substance>

A method (hereinafter, referred to as "method of the present invention") of the present invention for measuring a binding affinity between a nucleic acid and a test substance is simply required to include: a first measuring step for measuring fluorescence emitted in response to irradiation of light onto a first solution obtained by mixing a nucleic acid with an organic fluorescent substance which is capable of binding to an RNA and which emits fluorescence having an intensity greater while the organic fluorescent substance is liberated from the RNA than while the organic fluorescent substance is bound to the RNA; a second measuring step for measuring fluorescence emitted in response to irradiation of light onto a second solution obtained by further mixing the first solution with a test substance; and a comparing step for comparing (i) the fluorescence measured in the first measuring step with (ii) the fluorescence measured in the second measuring step.

The above organic fluorescent substance preferably includes: a compound represented by the following General Formula (1):

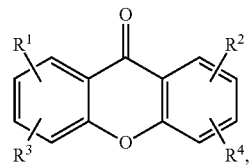

(1)

where each of $R^1$, $R^2$, $R^3$, and $R^4$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom; and/or a compound represented by the following General Formula (16):

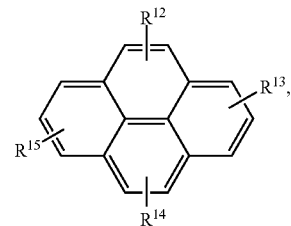

(16)

where each of $R^{12}$, $R^{13}$, $R^{14}$, and $R^{15}$ is independently a hydrogen atom, a hydroxyl group, or a C1 to C5 organic group which may contain one or more atoms selected from the group consisting of a hydrogen atom, a nitrogen atom, an oxygen atom, a sulfur atom, and a halogen atom.

The first solution prepared in the first step simply needs to be a solution in which the nucleic acid and the organic fluorescent substance such as a xanthone fluorescent molecule and/or a pyrene fluorescent molecule are dissolved. The first solution may be prepared with any solvent, provided that the solvent is capable of dissolving the nucleic acid, the test substance, and the organic fluorescent substance such as the xanthone fluorescent molecule and/or the pyrene fluorescent molecule. The solvent may be, e.g., the buffer solution mentioned in the above description of the composition of the present invention.

In the first measuring step, the fluorescence is measured by any method. Thus, the method is not particularly limited. The first solution is irradiated with light having a wavelength that causes, e.g., a liberated xanthone fluorescent molecule and/or pyrene fluorescent molecule to emit fluorescence. This causes the first solution to emit fluorescence, which is then measured. The light may be selected as appropriate in accordance with a kind of the xanthone fluorescent molecule and/or pyrene fluorescent molecule, and thus is not particularly limited to a specific one. The light has a wavelength, e.g., preferably within a range from 300 nm to 450 nm, or more preferably within a range from 350 nm to 400 nm. As described above, the method for measuring the fluorescence is not limited, provided that the method involves light irradiation and enables fluorescence detection. For example, the first solution is prepared in the wells of a microplate, and the fluorescence of the first solution is measured with use of a conventionally known microplate reader capable of light irradiation and fluorescence measurement.

The second solution prepared in the second measuring step is not limited, provided that the second solution is prepared by further dissolving, in the first solution, the test substance. The fluorescence in the second measuring step may be measured in the same manner as in the first measuring step.

In the comparing step, the fluorescence measured in the first step is compared with that measured in the second step. For example, the binding affinity between the nucleic acid and the test substance can be quantitatively measured by determining how much the intensity of the fluorescence emitted from the second solution is greater than that of the fluorescence emitted from the first solution.

The following describes a principle of the method of the present invention with reference to FIG. 1. FIG. 1 is a view schematically illustrating the principle of the method of the present invention. (a) of FIG. 1 schematically illustrates the first solution, whereas (b) of FIG. 1 schematically illustrates the second solution. FIG. 1 designates the xanthone fluorescent molecule simply as "FLUORESCENT MOLECULE".

As illustrated in (a) of FIG. 1, the first solution contains the xanthone fluorescent molecule mixed with the nucleic acid, and the xanthone fluorescent molecule is bound to the nucleic acid. The xanthone fluorescent molecule thus bound thereto emits little or no fluorescence in response to irradiation of light onto the first solution. In other words, the first measuring step detects no fluorescence or a fluorescence intensity having a low value. The fluorescence intensity obtained in this step depends on, e.g., a kind of the xanthone fluorescent molecule, a sequence of the nucleic acid, and respective amounts of the xanthone fluorescent molecule and the nucleic acid mixed.

As illustrated in (b) of FIG. 1, according to the method of the present invention, the second solution is then prepared by further mixing, in the first solution, a test substance. If the binding affinity between the test substance and the nucleic acid is higher than that between the xanthone fluorescent molecule and the nucleic acid, the xanthone fluorescent molecule is substituted with the test substance, so that the xanthone fluorescent molecule is liberated from the nucleic acid. The xanthone fluorescent molecule thus liberated emits fluorescence in response to irradiation of light thereon. Thus, the second measuring step measures the fluorescence emitted from the liberated xanthone fluorescent molecule.

According to the method of the present invention, the comparing step compares the fluorescence measured in the first measuring step with that measured in second measuring step. The comparison enables a measurement of the binding affinity between the test substance and the nucleic acid, on the basis of an increase by which the fluorescence measured in the second measuring step is larger than that measured in first measuring step. A large increase, for example, indicates a high binding affinity between the test substance and the nucleic acid. On the other hand, no detected increase in the fluorescence intensity indicates that the binding affinity between the test substance and the nucleic acid is lower than that between the xanthone fluorescent molecule and the nucleic acid.

The use of the xanthone fluorescent molecule is merely an example for explanation and the above description also applies to any other case involving use of a different organic fluorescent substance such as the pyrene fluorescent molecule.

As is clear from the above description, the present invention enables highly accurate and easy measurement of a binding affinity between a nucleic acid and a test substance. This in turn enables an inexpensive, quick, and easy screening of drugs. As described above, the method of the present invention can be implemented with use of, e.g., a conventionally known microplate and microplate reader capable of irradiating the microplate with excitation light so as to detect fluorescence. This allows the method of the present invention to be applied to individual candidate substances in a library one after another, or to such a plurality of candidate substances simultaneously. This consequently enables a high-throughput first screening of drugs.

The following presents examples to further describe the embodiment of the present invention in detail. The present invention is not limited to the examples below, and may thus be modified in its details to achieve various modes. In addition, the present invention is not limited to the description of the embodiment above, and may thus be altered by a skilled person within the scope of the claims. Any embodiment based on a proper combination of the technical means disclosed above is also encompassed in the technical scope of the present invention. All the patents mentioned above are incorporated herein by reference in their entirety.

EXAMPLES

Example 1

Synthesis of X2S

X2S was synthesized through the following synthetic pathway:

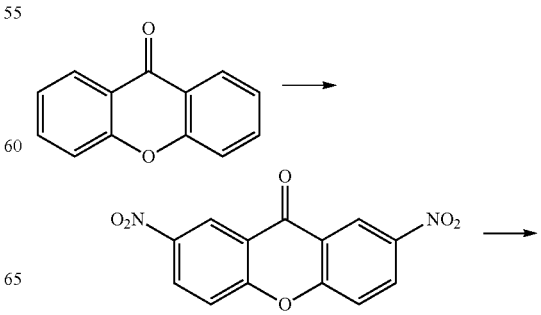

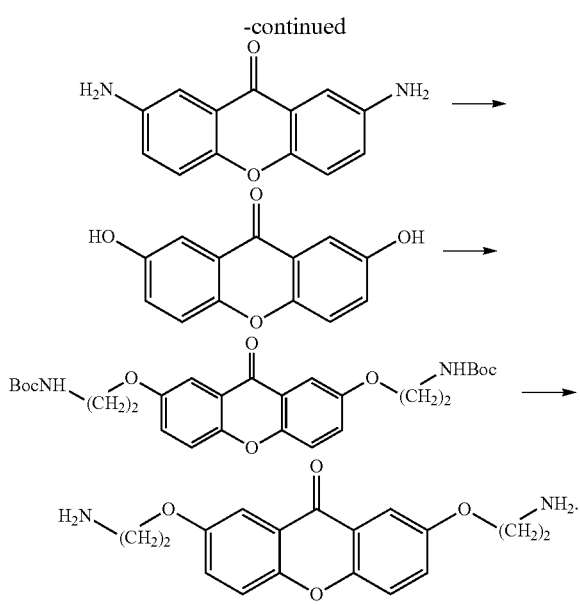

Specifically, 2,7-dihydroxyxanthone was first synthesized from xanthone as described in (i) Sergio H. Szajnman, Wen Yan, Brian N. Bailey, Roberto Docampo, Eleonora Elhalem, Juan B. Rodriguez., J. Med. Chem. 2000, 43, 1826-1840. and (ii) Tamara C. S. Pace, Sarah L. Monahan, Andrew I. MacRae, Monica Kaila, Cornelia Bohne., Photochemistry and Photobiology, 2006, 82:78-87.

Next, 2,7-dihydroxyxanthone (0.13 mmol, 30.0 mg) was dissolved in 7 ml of dry tetrahydrofuran (THF). Then, triphenylphosphine (86.3 mg, 0.33 mmol, 2.5 eq.) and diethyl azodicarboxylate (40% toluene solution, 143 mg, 150 μl, 0.33 mmol, 2.5 eq.) were added to the mixture. The resultant solution was stirred at room temperature for 15 minutes. After that, 2-amino-1-ethanol protected by an N-Boc group (53 mg, 50 μl, 0.33 mmol) was further added to the solution, which was then stirred at room temperature for 24 hours.

Subsequently, X2S protected by the N-Boc group (21.5 mg, 31%; hereinafter, referred to as "N-Boc-X2S") was obtained through purification by column chromatography (hexane:ethyl acetate=5:1, then $CHCl_3:CH_3OH=100:1-2$). NMR of N-Boc-X2S provided the following results: $^1$HNMR ($CDCl_3$) 1.35-1.45 (9H); 3.52-3.54 (2H); 4.03-4.09, (2H); 4.90-4.96 (broad 1H); 7.25-7.28, 1H, 7.37-7.39, (d, 1H, J=9.04 Hz); 7.61-7.62 (d, 1H, J=2.92 Hz). $^{13}$CNMR: 28.886, 29.686, 40.003, 67.884, 106.840, 119.485, 121.468, 124.824, 151.102, 154.796, 155.824, 176.721; HR-MS: Calcd. for $C_{27}H_{34}N_2NaO_8$ [M+Na]+, 537.2213; found, 537.2189.

The N-Boc group was removed as follows: First, N-Boc-X2S was mixed in 15 ml of ethyl acetate. Next, 4N HCl was further added to the mixture. The resultant mixture was then stirred at room temperature for 15 minutes. After that, the solution obtained as a result of the stirring was concentrated. The resultant product was then dissolved in pure water. The solution thus obtained was filtered, and the residue was freeze-dried. This provided X2S in the form of a white solid. The white solid was dissolved in pure water and stored as a 1-mM X2S solution for use in the Examples below. HR-MS spectrometry of the X2S obtained as above provided the following results: HR-MS: [M+H]+315.1334, calculated $C_{17}H_{19}N_2O_4$, 315.1345.

The above synthesis was performed with reference to (i) Szajnman, S. H.; Yan, W.; Bailey, B. N.; Docampo, R.; Elhalem, E.; Rodriguez, J. B. J. Med. Chem. 2000, 43, 1826-1840., and (ii) Pace, T. C. S.; Monahan, S. L.; MacRae, A. I.; Kaila, M.; Bohne, C. Photochem. Photobiol. 2006, 82, 78-87.

Example 2

Evaluation of Binding Between X2S and RNA

Figure 2:
FIG. 2
FIG. 2 is a view schematically illustrating the structure of an RNA used in Examples of the present invention.

Next, binding between X2S and RNAs was evaluated. The RNAs used in the present example had the structure illustrated in FIG. 2. FIG. 2 is a diagram schematically illustrating the structure of the RNAs used in the present example. The RNAs used in the present example had sequences shown in SEQ ID NOs: 1 through 3.

The symbol N in FIG. 2 represents either a base out of A, U, C, and G, or no base. Thus, in a case where a particular RNA as in FIG. 2 has N representing a base out of A, U, C, and G, the RNA is an RNA formed by hybridization of an RNA having the base sequence shown in SEQ ID NO: 1 with a single strand RNA having the base sequence shown in SEQ ID NO: 2. On the other hand, in a case where a particular RNA as in FIG. 2 has N representing no base, the RNA is an RNA formed by hybridization of an RNA having the base sequence shown in SEQ ID NO: 1 with an RNA having the base sequence shown in SEQ ID NO: 3.

According to the RNAs used in the present example, in the case where N represents a base out of A, U, C, and G, the base does not bind to a complementary base. This results in formation of a bulge structure. In the case where N represents no base, the RNA does not have a bulge structure. In a case where N represents A, which then does not bind to a complementary base, the RNA has a bulge structure, which is herein also referred to as "A bulge". This also applies to other bases. The RNAs used in the present example were purchased from Hokkaido System Science Co., Ltd.

Firstly, X2S was mixed in a cacodylate buffer solution (sodium cacodylate: 10 mM, pH 7.0; NaCl: 100 mM) at 10 μM, so that an X2S solution was obtained. The X2S solution was irradiated with light having an absorption maximum of 371±3 nm, and a fluorescence intensity was then measured. The fluorescence intensity was measured with use of a device (product number: RF-5300PC) available from Shimadzu Corporation. For each type of the RNAs, the fluorescence intensity was measured after the RNA was mixed in the X2S solution at 30 μM.

Figure 3:
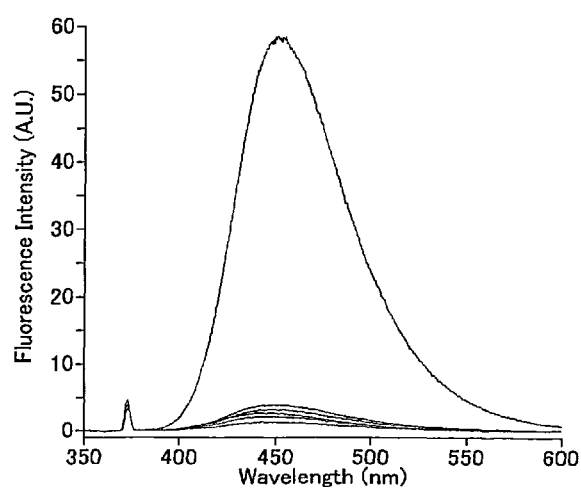
FIG. 3
FIG. 3 is a view illustrating a result of evaluation of binding between X2S and RNA.
Figure 4:
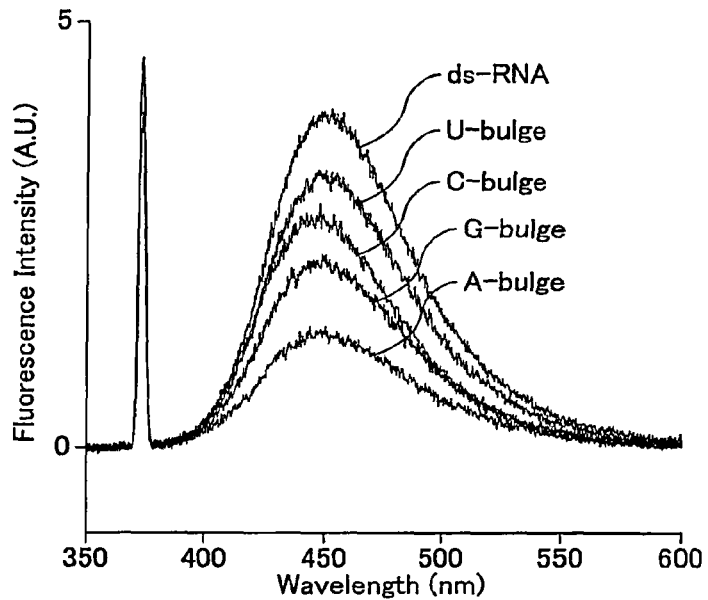
FIG. 4
FIG. 4 is a view illustrating a result of evaluation of binding between X2S and RNA.

FIGS. 3 and 4 compare the fluorescence intensities measured before and after the RNA was mixed. FIGS. 3 and 4 both evaluate the binding between X2S and the RNA. The horizontal axis represents the fluorescence wavelength, whereas the vertical axis represents the fluorescence intensity. FIG. 4 is an enlarged graph corresponding to the fluorescence intensity of 5 A.U. in FIG. 3 and its vicinity.

FIGS. 3 and 4 verify that although the fluorescence intensities slightly vary depending on (i) whether or not the bulge structure is present and (ii) a kind of the base causing the bulge structure to form, X2S is capable of binding to RNAs having various structures.

Example 3

Evaluation of Binding Between X1S and RNA

Figure 5:
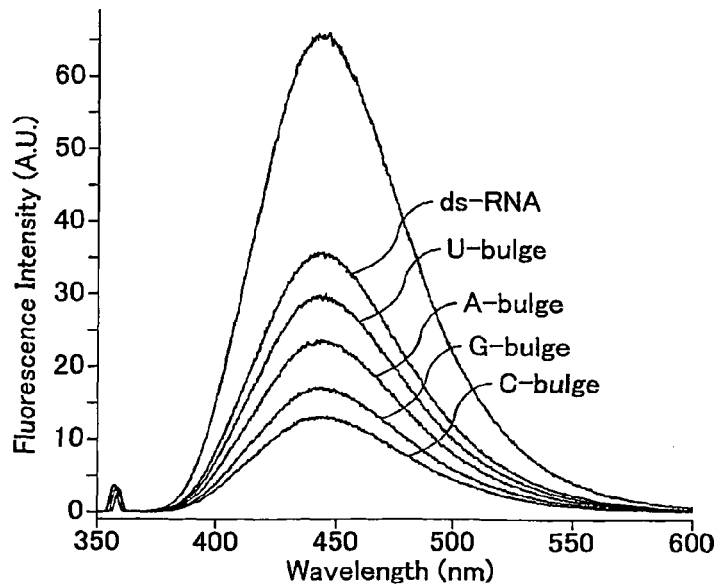
FIG. 5
FIG. 5 is a view illustrating a result of evaluation of binding between X1S and RNA.

Binding between X1S and RNAs was evaluated by a method identical to the method described in Example 2, except that X1S was used instead of X2S. A result is shown in FIG. 5. FIG. 5 is a graph illustrating the result of the evaluation of binding between X1S and RNAs. The horizontal axis represents the fluorescence wavelength, whereas the vertical axis represents the fluorescence intensity.

FIG. 5 verifies that X1S as well as X2S binds to RNAs regardless of whether the bulge structure is present. A detected decrease in the fluorescence intensity was small as compared to the case of X2S.

The following describes how X1S used in the present example was synthesized. The synthesis of X1S was performed through the following synthetic pathway:

rated, the solution was purified by column chromatography (hexane:ethyl acetate=4:1, then $CHCl_3$:MeOH=100:1-3). A solvent of the solution thus obtained was evaporated off. The remaining product was dried with a high-vacuum pump. This provided 68.9 g (yield of 57.1%) of a compound 5. NMR of the compound 5 provided the following results: $^1$HNMR (d-$CDCl_3$, 400M): 1.39 (s, 9H); 3.52, m, 2H, 4.03-4.08, m, 2H, 4.92, broad, NH; 7.31-7.38, m, 2H; 7.41-7.49, m, 2H, 7.68-7.77, m, 2H, 8.31-8.34, m, 1H. $^{13}$CNMR, 39.984,

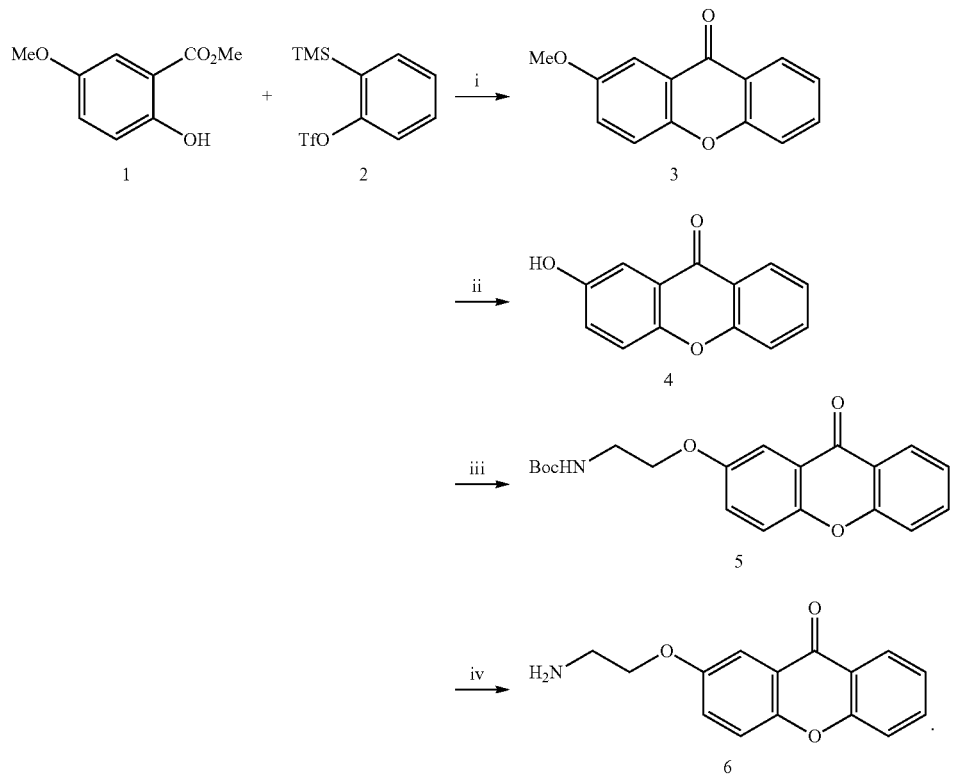

In this synthetic pathway for X1S, a compound 3 was synthesized (reaction i) from compounds 1 and 2 by a method described in Org. Lett. 2005, Vol 7, No. 19, 4273-4275.

In a subsequent reaction ii, first, a mixture of 150 mg (0.644 mmol) of the compound 3 (2-methoxyxanthone) and 1.8 g of pyridine hydrochloride was heated at 180° C. for 10 hours. Next, the mixture was cooled to room temperature and then mixed in 50 ml of water. After that, the mixture was filtered, so that a white solid was obtained. The white solid was washed with water and then dried with a high-vacuum pump, so that 96.1 mg of a white substance was obtained. This provided a compound 4 (2-hydroxyxanthone) at a yield of 67.0%. NMR of this 2-hydroxyxanthone provided the following results: $^1$HNMR (d-DMSO, 400M): 7.30-7.33, m, 1H, 7.43-7.47, m, 2H, 7.54-7.56, d, 1H, 7.62-7.64,d,1H, 7.82-7.86,m,1H, 8.16-8.18, d,1H, 9.97, s, 1H. HR-MS: [M+H]+ 213.05506, calculated C18H9O3: 213.05517.

In a subsequent reaction iii, first, 72 mg (0.340 mmol) of the compound 4 (2-hydroxyxanthone), 54.8 mg (52 µl, 0.340 mmol) of Boc $NHCH_2CH_2OH$, and 91.8 mg (0.34 mmol) of $Ph_3P$ were dissolved in 5 ml of THF. DEAD (40% toluene solution, 148.5 mg, 155 µl, 0.341 mmol) dissolved in 2 ml of THF was slowly added to the above solution. The resultant solution was stirred for 24 hours. After the THF was evapo- 67.851, 107.037, 109.873, 117.962, 119.491, 121.192, 122.096, 123.658, 123.782, 124.826, 126.618, 126.683, 134.674, 151.114, 154.879, 156.112, 177.041.

Finally, in a subsequent reaction iv, first, the compound 5 obtained through the reaction iii was mixed in 15 ml of 4N HCl ethyl acetate. The mixture was stirred at room temperature for 15 minutes. Next, the ethyl acetate was evaporated off, and the resultant final product was mixed in water. After that, the product was filtered and then freeze-dried, so that X1S in the form of a white solid was obtained. This X1S was dissolved in pure water and stored as a 1-mM X1S solution for use in the Examples above. HR-MS spectrometry of the X2S obtained as above provided the following results: HR-MS: 256.09874, calculated: C15H14NO3, 256.09737.

Example 4

Evaluation of Binding Between X2S and RRE

In this Example, binding between RRE and X2S was evaluated by a method identical to the method in Example 2.

Figure 6:
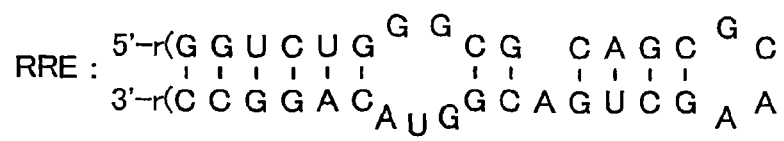
FIG. 6
FIG. 6 is a view schematically illustrating the structure of RRE used in Examples of the present invention.

The amino acid sequence of RRE is shown in SEQ ID NO: 8. Further, the structure of RRE is shown in FIG. 6. FIG. 6 schematically shows the structure of RRE. As shown in FIG.

6, RRE has a U-bulge structure. RRE was purchased from Hokkaido System Science Co., Ltd.

Firstly, the X2S solution obtained in Example 1 was diluted with a cacodylate buffer solution (sodium cacodylate: 10 mM, pH 7.0; NaCl: 100 mM), so that a concentration of X2S became 2 μM. To the 2-μM X2S solution thus obtained, RRE was added in steps at 0 μM, 1 μM, 2 μM, 3 μM, 4 μM, 5 μM, 6 μM, and 8 μM. Further, a fluorescence intensity of the 2-μM X2S solution was measured at each concentration. The fluorescence intensity was measured in the same manner as in Example 2.

A result of the measurement is shown in FIGS. 7 and 8. FIG. 7 is a view illustrating a result of evaluation of binding between X2S and RRE. In FIG. 7, the horizontal axis represents the fluorescence wavelength, whereas the vertical axis represents the fluorescence intensity. The direction of the arrow in FIG. 7 shows an increasing order of concentrations of RRE at which the respective curved lines were obtained. That is, the curved line at the top shows a result obtained at a concentration of 0 μM of RRE, and the curved line at the bottom shows a result obtained at a concentration of 8 μM of RRE. Other figures include such arrows for results of measurements of fluorescence intensities. The direction of each of such arrows also shows an increasing order of an amount of a substance which was added in steps.

FIG. 8 is a view plotting the fluorescence intensities at a measured wavelength of 453 nm shown in the result illustrated in FIG. 7. The horizontal axis represents the concentration of RRE, whereas the vertical axis represents the fluorescence intensity.

FIG. 7 and FIG. 8 show that the fluorescence intensity was reduced as the concentration of the RNA increased. Further, as shown in FIG. 8, the concentration of RNA was correlated with the fluorescence intensity (correlation coefficient: R=0.98), and a correlation curve was formed. These verify that, once X2S binds to an RNA, fluorescence of X2S is quenched.

Example 5

Displacement Assay Using X2S

In this Example, X2S was used to measure a binding affinity between a test substance and RRE. As the test substance, Rev protein (supplied by Professor Takashi MORII, Graduates School of Energy Science, Kyoto University), aminoglycoside antibiotic neomycin (available from Sigma-Aldrich, product number; N-1876) (hereinafter, simply referred to as "neomycin"), and thrombin (available from Bachem, product number; AG H-8550) were used. It is known that Rev protein and neomycin bind to RRE, and that thrombin does not bind to RRE. The structure of Rev protein is shown in FIG. 9, and the amino acid sequence of Rev protein is shown in SEQ ID NO: 5. FIG. 9 is a view schematically illustrating the structure of Rev protein. Further, the structure of thrombin is shown in FIG. 10, and the amino acid sequence of thrombin is shown in SEQ ID NO: 6. FIG. 10 is a view schematically illustrating the structure of thrombin.

Firstly, in the same manner as in Example 3, X2S and RRE were dissolved in a cacodylate buffer solution (sodium cacodylate: 10 mM, pH 7.0; NaCl: 100 mM) each at 2 μM. Thus, an X2S-RRE solution was prepared.

To the X2S-RRE solution, Rev protein was added in steps at 0 μM, 0.4 μM, 0.8 μM, 1.2 μM, 1.6 μM, 2.0 μM, 2.4 μM, 2.8 μM, 3.2 μM, 3.6 μM, and 4.0 μM. Further, a fluorescence intensity was measured at each concentration. Similarly, to the X2S-RRE solution, neomycin was added in steps at 0 μM, 0.4 μM, 0.8 μM, 1.2 μM, 1.6 μM, 2.0 μM, 2.4 μM, 2.8 μM, 3.2 μM, 3.6 μM, and 4.0 μM. Further, a fluorescence intensity was measured at each concentration. Similarly, to the X2S-RRE solution, thrombin was added in steps at 0 μM, 0.4 μM, 0.8 μM, 1.2 μM, 1.6 μM, 2.0 μM, 2.4 μM, 2.8 μM, 3.2 μM, 3.6 μM, and 4.0 μM. Further, a fluorescence intensity was measured at each concentration. The fluorescence intensities were measured in the same manner as that described in Example 2.

Figure 13:
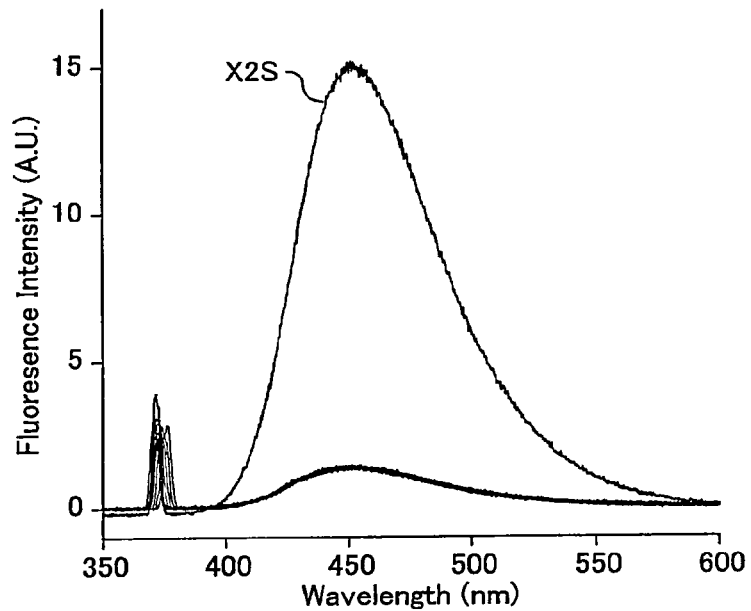
FIG. 13
FIG. 13 is a view illustrating a result of a measurement of a binding affinity between thrombin and RRE.

Results of the measurements are shown in FIGS. 11 to 14. FIG. 11 is a view illustrating a result of the measurement of a binding affinity between Rev protein and RRE; FIG. 12 is a view illustrating a result of the measurement of a binding affinity between neomycin and RRE; and FIG. 13 is a view illustrating a result of the measurement of a binding affinity between thrombin and RRE. In each of FIGS. 11 to 13, the horizontal axis represents the fluorescence wavelength, whereas the vertical axis represents the fluorescence intensity. Further, the curved line at the top shows a fluorescence intensity detected in the absence of RRE, and the curved line at the bottom shows a fluorescence intensity detected in the presence of RRE and X2S but in the absence of the test substance. Furthermore, along the direction of the arrow extending from the curved line at the bottom, the curved lines are arranged in order of increasing amount of the test substance which was added.

Figure 14:
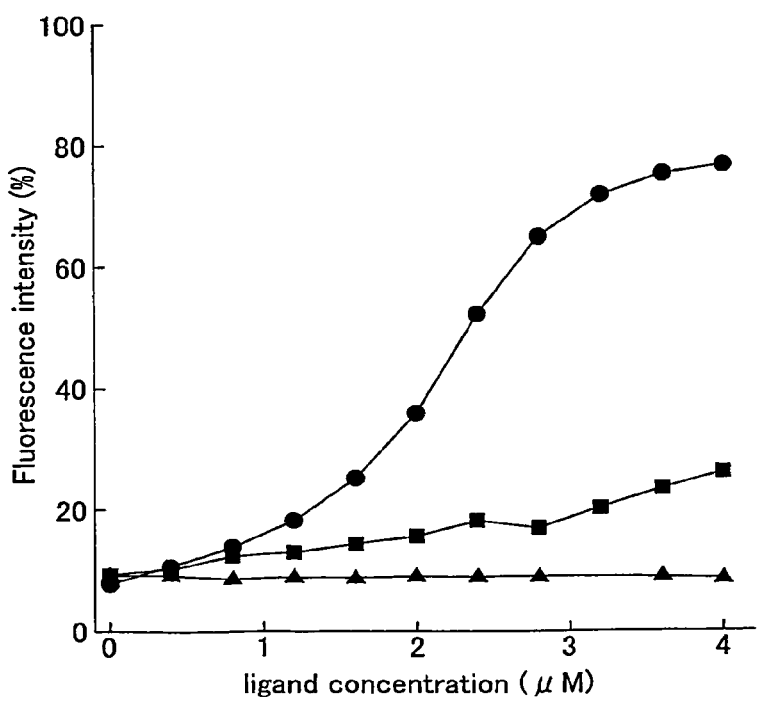
FIG. 14
FIG. 14 is a view plotting the fluorescence intensities at a fluorescence wavelength of 453 nm shown in the results illustrated in FIGS. 11 to 13.

FIG. 14 is a view plotting the fluorescence intensities at a fluorescence wavelength of 453 nm shown in the results illustrated in FIGS. 11 to 13. The horizontal axis represents the concentration of each test substance, whereas the vertical axis represents the fluorescence intensity. In FIG. 14, the circle marks represent the result obtained in the case involving use of Rev protein, the square marks represent the result obtained in the case involving use of neomycin, and the triangle marks represent the result obtained in the case involving use of thrombin.

FIGS. 11 and 14 show that the addition of Rev protein increased the fluorescence intensity. This shows that, as Rev protein increased, Rev protein bound to RRE in place of X2S which had bound to RRE, and consequently X2S was liberated from RRE. This shows that Rev protein has a significantly high binding affinity with respect to RRE.

FIGS. 12 and 14 show that, although the addition of neomycin slightly increased the fluorescence intensity, the degree of the increase in the fluorescence intensity was smaller than that observed in the case where Rev protein was added. This shows that, although neomycin binds to RRE, neomycin has a lower binding affinity with respect to RRE compared with Rev protein.

FIGS. 13 and 14 show that the addition of thrombin hardly increased the fluorescence intensity. This verifies that thrombin does not bind to RRE.

Thus, it was verified that the present invention is capable of measuring a binding affinity of various substances to be examined with respect to a nucleic acid.

Further, FIG. 14 shows that the fluorescence intensity recovered to approximately 80%. Considering a known fact that Rev protein binds to a U-bulge structure of RRE, it can be said that this shows X2S's dominant binding to a bulge structure of RRE.

Example 6

Comparison Between X2S and Ethidium Bromide

In this Example, as a comparative example, binding between ethidium bromide and RRE was evaluated, and a displacement assay using ethidium bromide was performed. Then, results obtained were compared with those obtained in the case involving use of X2S.

(Evaluation of Binding Between Ethidium Bromide and RRE)

To a 2-μM ethidium bromide solution, RRE was added at 0 μM, 1 μM, 2 μM, 3 μM, 4 μM, 5 μM, 6 μM, and 7 μM. Further, fluorescence was detected at each concentration of RRE, which fluorescence was emitted in response to irradiation of excitation light having a wavelength of 284 nm. A fluorescence intensity was measured in the same manner as in Example 2, except that the wavelength of excitation light was different between this Example and Example 2.

Figure 15:
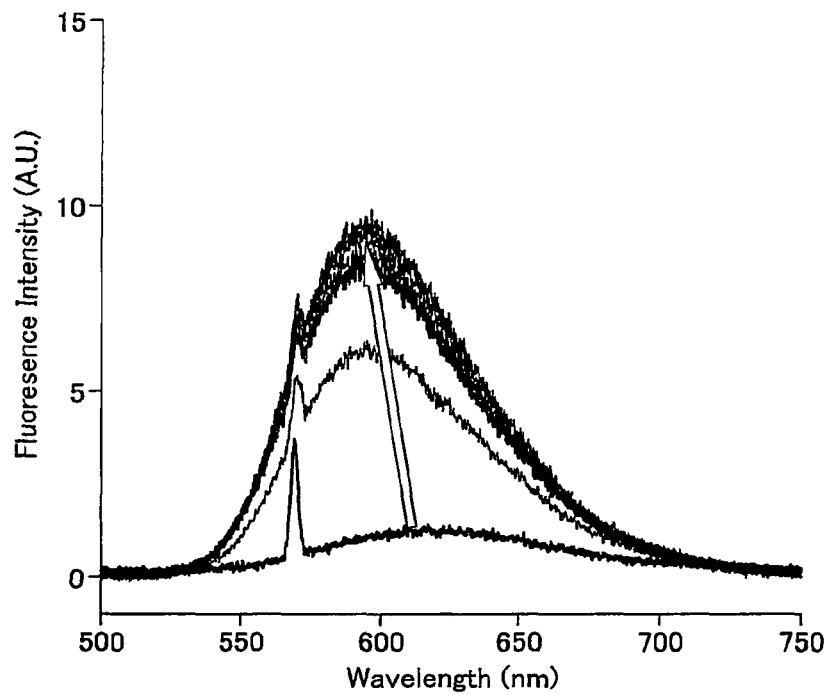
FIG. 15
FIG. 15 is a view illustrating a result of evaluation of binding between RRE and ethidium bromide.

A result of the measurement is shown in FIG. 15. FIG. 15 is a view illustrating a result of evaluation of binding between RRE and ethidium bromide. The horizontal axis represents the fluorescence wavelength, whereas the vertical axis represents the fluorescence intensity.

FIG. 15 shows that the fluorescence increased as the concentration of RRE increased. Further, at the point that the amount of ethidium bromide was equal to that of RRE (each at 2 μM), an amount of increase in fluorescence intensity decreased and saturated. As is clear from comparison between this result and the result shown in FIG. 11, a change in the fluorescence intensity was greater in the case involving use of X2S than in the case involving use of ethidium bromide.

(Comparison Between Displacement Assay Using X2S and Displacement Assay Using Ethidium Bromide)

A displacement assay using X2S was performed in the same manner as that described in Example 5, except that, in this Example, fluorescence was measured also when Rev protein was added at concentrations of 4.4 μM and 4.8 μM.

Figure 16:
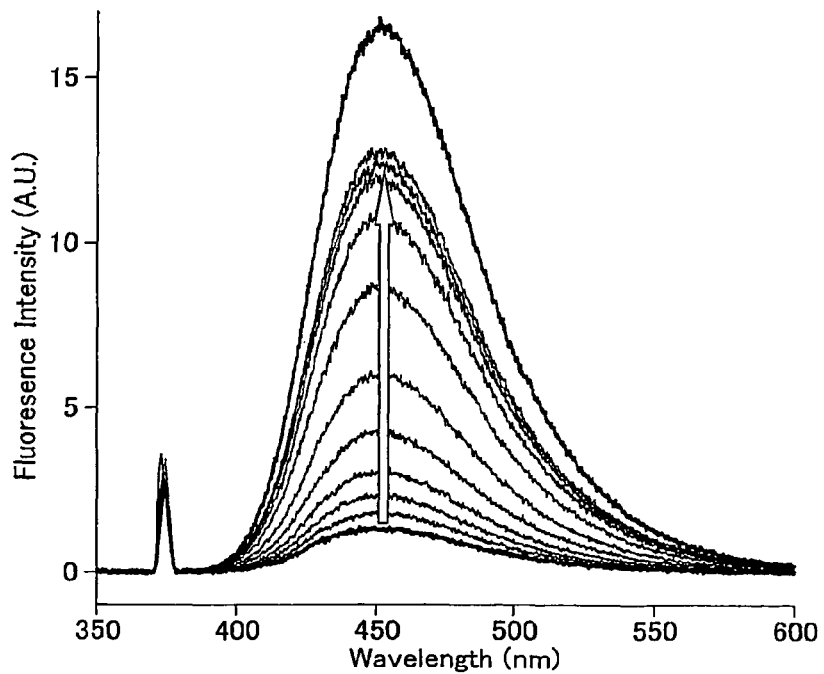
FIG. 16
FIG. 16 is a view illustrating a result of a displacement assay using X2S.

A result of the displacement assay is shown in FIG. 16. FIG. 16 is a view illustrating the result of the displacement assay using X2S. The horizontal axis represents the fluorescence wavelength, whereas the vertical axis represents the fluorescence intensity.

A displacement assay using ethidium bromide was performed in the same manner as that described in Example 5. However, the displacement assay performed herein differed from that performed in Example 5 in the following points: Instead of X2S, ethidium bromide was used; Fluorescence was measured also when Rev protein was added at concentrations of 4.4 μM and 4.8 μM; A wavelength of excitation light for a measurement of fluorescence was set to 284 nm.

Figure 17:
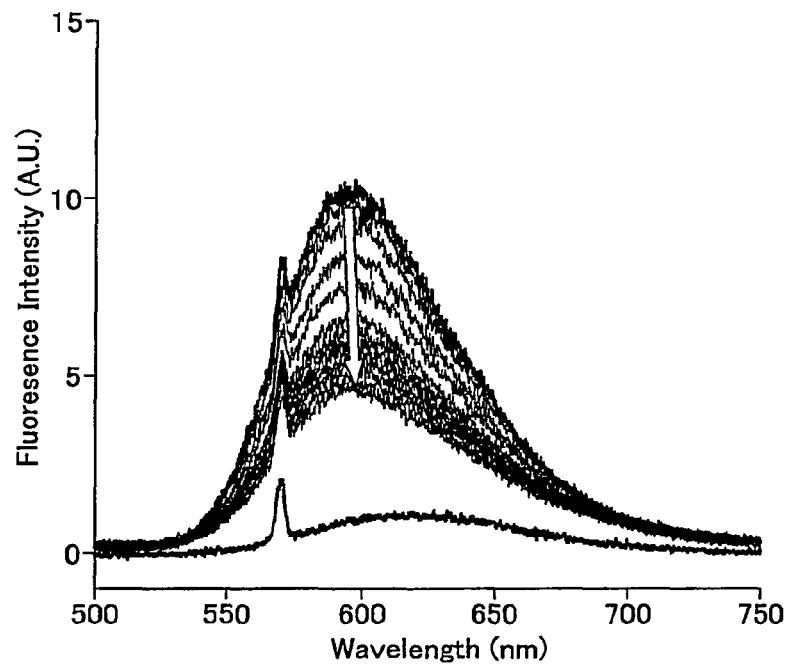
FIG. 17
FIG. 17 is a view illustrating a result of a displacement assay using ethidium bromide.

A result of the displacement assay is shown in FIG. 17. FIG. 17 is a view illustrating the result of the displacement assay using ethidium bromide. The horizontal axis represents the fluorescence wavelength, whereas the vertical axis represents the fluorescence intensity.

FIGS. 16 and 17 show the following: The fluorescence was reduced as ethidium bromide increased. However, once the fluorescence intensity was reduced to approximately 30% of an initial value at a concentration of 2.4 μM of RRE, a degree of the increase in the fluorescence intensity became gentle, so that the fluorescence intensity was ultimately reduced by approximately 60%. On the other hand, in the case involving use of X2S, a reduction in the fluorescence intensity was clearly observed even at a concentration 3.2 μM of RRE, and the fluorescence intensity ultimately increased by approximately 80%.

These results show that use of X2S makes it possible to measure a binding affinity between an RNA and a test substance with extremely high accuracy.

Example 7

Binding Between X2S and Single Strand RNA

In this Example, binding between X2S and a single strand RNA (hereinafter, referred to as "ssRNA") was evaluated. Specifically, the evaluation was performed in the same manner as that described in Example 2. However, the evaluation performed in this Example differed from that performed in Example 2 in the following points: Instead of the double strand RNA, an ssRNA was used; The ssRNA was added in steps at 0 μM, 1 μM, 2 μM, 3 μM, 4 μM, 5 μM, 6 μM, 7 μM, and 8 μM; The ssRNA was purchased from: Hokkaido System Science Co., Ltd. The sequence of the ssRNA is shown in SEQ ID NO: 7.

Figure 18:
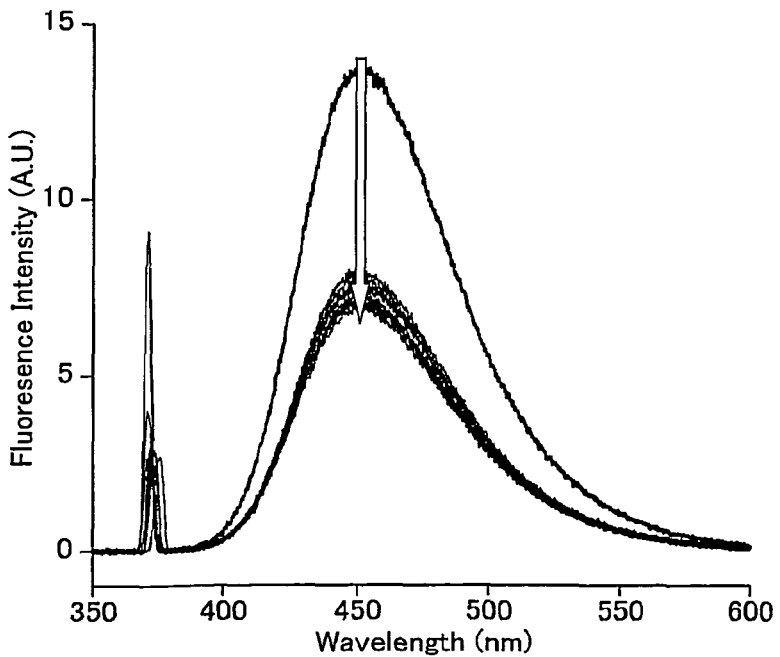
FIG. 18
FIG. 18 is a view illustrating a result of evaluation of binding between X2S and ssRNA.

A result of the evaluation is shown in FIG. 18. FIG. 18 is a view illustrating the result of the evaluation of binding between X2S and the ssRNA. The horizontal axis represents the fluorescence wavelength, whereas the vertical axis represents the fluorescence intensity.

FIG. 18 verifies that X2S also binds to an ssRNA. Further, the fluorescence intensity observed at a concentration of 0 μM of the ssRNA was compared with that observed at a concentration of 8 μM of the ssRNA. The comparison showed that an amount of change therebetween was approximately 50%.

Example 8

Synthesis of X2S(3)

A compound represented by the above General Formula (12) (where n=3) i.e., 2,7-bis(2-aminopropoxy)xanthen-9-one (hereinafter, referred to as "X2S(3)") was synthesized. Firstly, 2,7-dihydroxyxanthone was synthesized by a method identical to the method in Example 1. Next, 2,7-dihydroxyxanthone (2.85 mmol, 650 mg) was dissolved in 30 ml of dry THF (tetrahydrofuran). Then, triphenylphosphine (1600 mg, 6.10 mmol, 2.1 eq.) and diethyl azodicarboxylate (40% toluene solution, 2800 mg, 2900 μl, 6.35 mmol, 2.2 eq.) were added to the mixture. The resultant solution was stirred at room temperature for 15 minutes. After that, 3-amino-1-ethanol (1100 mg, 6.28 mmol) protected by an N-Boc group was added to the solution, which was then stirred at room temperature for 24 hours.

Subsequently, X2S(3) protected by the N-Boc group (hereinafter, referred to as "N-Boc-X2S(3)") (278 mg, yield: 18%) was obtained through purification by column chromatography performed in the same manner as in Example 1. N-Boc-X2S(3) thus obtained was evaluated by means of NMR, and a result thereof is shown in Table 1.

The N-Boc group was removed by a method identical to the method described in Example 1, so that a white solid of X2S(3) was obtained. The white solid was dissolved in pure water and stored as a 1-mM X2S(3) solution for use in the Examples below. X2S(3) obtained was subjected to MS spectrometry, and a result thereof is shown in Table 1.

TABLE 1

| Ex. | Structure | Yield (%) | Spectrum Data: NMR 1H-NMR (CDCl3, TMS, 600 MHz, ppm) | Spectrum Data: MS |
|---|---|---|---|---|
| 8 | N-Boc-X2S(3) | 18 | δ = 1.44-1.46 (9H), 1.99-2.06 (2H), 3.36-3.38 (2H), 4.12-4.16 (2H), 4.75-4.82 (broad 1H), 7.31-7.33 (1H), 7.42-7.44 (d, 1H, J = 9.18 Hz), 7.67-7.68 (d, 1H, J = 2.94 Hz) | MS (FAB) m/Z = 542 [M$^+$] |
| 9 | N-Boc-X2S(4) | 28 | δ = 1.44-1.47 (9H), 1.68-1.84 (2H), 1.85-1.90 (2H), 3.21-3.24 (2H), 4.09-4.11 (2H), 4.62-4.67 (broad 1H), 7.31-7.33 (1H), 7.42-7.44 (d, 1H, J = 9.18 Hz), 7.67-7.68 (d, 1H, J = 2.94 Hz) | MS (FAB) m/Z = 571 [M + H$^+$] |
| 10 | N-Boc-X2S(5) | 44 | δ = 1.44-1.46 (9H), 1.51-1.61 (4H), 1.83-1.88 (2H), 3.15-3.19 (2H), 4.07-4.09 (2H), 4.53-4.60 (broad 1H), 7.31-7.33 (1H), 7.42-7.44 (d, 1H, J = 9.18 Hz), 7.67-7.68 (d, 1H, J = 2.94 Hz) | MS (FAB) m/Z = 599 [M + H$^+$] |
| 11 | N-Boc-3,6-X2S(2) | 20 | δ = 1.4-1.49 (9H), 3.53-3.63 (2H), 4.09-4.17 (2H), 7.30-7.35 (dd, 1H, J = 2.92, 9.04), 7.42-7.47 (d, 1H, J = 9.04 Hz), 7.66-7.69 (d, 1H, J = 2.92 Hz) | MS (ESI) [M + Na]$^+$ = 537 |
| 12 | N-Boc-X2S(2-Me) | 21 | δ = 1.33-1.34 (3H), 1.47-1.49 (9H), 4.10-4.17 (broad 1H), 4.04-4.05 (2H), 4.77-4.64 (broad 1H), 7.34-7.36 (1H), 7.44-7.45 (d, 1H, 9.18 Hz), 7.67-7.68 (d, 1H, J = 2.94 Hz) | MS (FAB) m/Z = 543 [M + H$^+$] |

Abbreviation:
"Ex." stands for "Example".

Example 9

Synthesis of X2S(4)

A compound represented by the above General Formula (12) (where n=4) i.e., 2,7-bis(2-aminobutoxy)xanthen-9-one (hereinafter, referred to as "X2S(4)") was synthesized. Firstly, 2,7-dihydroxyxanthone was synthesized by a method identical to the method in Example 1. Next, 2,7-dihydroxyxanthone (3.94 mmol, 900 mg) was dissolved in 60 ml of dry THF (tetrahydrofuran). Then, triphenylphosphine (2230 mg, 8.50 mmol, 2.2 eq.) and diethyl azodicarboxylate (40% toluene solution, 3700 mg, 3900 µl, 8.58 mmol, 2.2 eq.) were added to the mixture. The resultant solution was stirred at room temperature for 15 minutes. After that, 4-amino-1-ethanol protected by an N-Boc group (1650 mg, 8.72 mmol) was added to the solution, which was then stirred at room temperature for 24 hours.

Next, X2S(4) protected by the N-Boc group (hereinafter, referred to as "N-Boc-X2S(4)") (630 mg, yield: 28%) was obtained through purification by column chromatography performed in the same manner as in Example 1. N-Boc-X2S (4) thus obtained was evaluated by means of NMR, and a result thereof is shown in Table 1.

The N-Boc group was removed in the same manner as that described in Example 1, so that a white solid of X2S(4) was obtained. The white solid was dissolved in pure water and stored as a 1-mM X2S(4) solution for use in the Examples below. X2S(4) obtained was subjected to MS spectrometry, and a result thereof is shown in Table 1.

Example 10

Synthesis of X2S(5)

A compound represented by the above General Formula (12) (where n=5) i.e., 2,7-bis(2-aminopentoxy)xanthen-9-one (hereinafter, referred to as "X2S(5)") was synthesized. Firstly, 2,7-dihydroxyxanthone was synthesized by a method identical to the method in Example 1. Next, 2,7-dihydroxyxanthone (3.51 mmol, 800 mg) was dissolved in 60 ml of dry THF (tetrahydrofuran). Then, triphenylphosphine (2000 mg, 7.63 mmol, 2.2 eq.) and diethyl azodicarboxylate (40% toluene solution, 3300 mg, 3500 µl, 7.66 mmol, 2.2 eq.) were added to the mixture. The resultant solution was stirred at room temperature for 15 minutes. After that, 5-amino-1-ethanol (1500 mg, 7.38 mmol) protected by an N-Boc group was added to the solution, which was then stirred at room temperature for 24 hours.

Subsequently, X2S(5) protected by the N-Boc group (hereinafter, referred to as "N-Boc-X2S(5)") (924 mg, yield: 44%) was obtained through purification by column chromatography performed in the same manner as in Example 1. N-Boc-X2S(5) thus obtained was evaluated by means of NMR, and a result thereof is shown in Table 1.

The N-Boc group was removed in the same manner as that described in Example 1, so that a white solid of X2S(5) was obtained. The white solid was dissolved in pure water and stored as a 1-mM X2S(5) solution for use in the Examples below. X2S(5) obtained was subjected to MS spectrometry, and a result thereof is shown in Table 1.

Example 11

Synthesis of 3,6-X2S(2)

A compound represented by Structural Formula (13) i.e., 3,6-bis(2-aminoethoxy)xanthen-9-one (hereinafter, referred to as "3,6-X2S(2)") was synthesized.

2,2',4,4'-tetrahydroxybenzophenone (0.010 mmol, 2.5 g) was suspended in 20 ml of water, which was then stored in an airtight container and heated at 200° C. for 4 hours in an autoclave. The solution was subjected to vacuum filtration, so as to yield a solid. The solid was washed with methanol and ethyl acetate, so that 3,6-X2S(2) (1.7 g, yield: 73%) was obtained.

Next, 3,6-dihydroxyxanthone (0.32 mmol, 72 mg) was dissolved in 3.5 ml of dry THF (tetrahydrofuran). Then, triphenylphosphine (210 mg, 0.80 mmol, 2.5 eq.) and DEAD (2.2M 40% toluene solution, 364 µl, 0.80 mmol, 2.5 eq.) were added to the mixture. The resultant solution was stirred at room temperature for 45 minutes. After that, ethanolamine protected by an N-Boc group (129 mg, 0.80 mmol) was added to the solution, which was then stirred at room temperature for 24 hours. Further, triphenylphosphine (84 mg, 0.32 mmol, 1.0 eq.) and DEAD (2.2M 40% toluene solution, 145 µl, 0.32 mmol, 1.0 eq.) were added to the solution, which was then stirred for 24 hours.

Subsequently, 3,6-X2S(2) protected by the N-Boc group (hereinafter, referred to as "N-Boc-3,6-X2S(2)") (32.3 mg, yield: 20%) was obtained through purification by column chromatography performed in the same manner as in Example 1 and GPC. N-Boc-3,6-X2S(2) thus obtained was evaluated by means of NMR, and a result thereof is shown in Table 1.

The N-Boc group was removed in the same manner as that described in Example 1, so that a white solid of 3,6-X2S(2) was obtained. The white solid was dissolved in pure water and stored as a 1-mM 3,6-X2S(2) solution for use in the Examples below. 3,6-X2S(2) obtained was subjected to MS spectrometry, and a result thereof is shown in Table 1.

Example 12

Synthesis of X2S(2-Me)

A compound represented by General Formula (15) (where n=1) i.e. 2,7-bis(2-methyl-2-aminoethoxy)xanthen-9-one (hereinafter, referred to as "X2S(2-Me)") was synthesized. Firstly, 2,7-dihydroxyxanthone was synthesized by a method identical to the method in Example 1. Next, 2,7-dihydroxyxanthone (3.51 mmol, 800 mg) was dissolved in 50 ml of dry THF (tetrahydrofuran). Then, triphenylphosphine (2000 mg, 7.63 mmol, 2.2 eq.) and diethyl azodicarboxylate (40% toluene solution, 3300 mg, 3500 µl, 7.66 mmol, 2.2 eq.) were added to the mixture. The resultant solution was stirred at room temperature for 15 minutes. After that, 2-amino-1-propanol (1340 mg, 7.65 mmol) protected by an N-Boc group was added to the solution, which was then stirred at room temperature for 24 hours.

Next, X2S(2-Me) protected by the N-Boc group (hereinafter, referred to as "N-Boc-X2S(2-Me)") (399 mg, yield: 21%) was obtained through purification by column chromatography performed in the same manner as in Example 1. N-Boc-X2S(2-Me) thus obtained was evaluated by means of NMR, and a result thereof is shown in Table 1.

The N-Boc group was removed in the same manner as that described in Example 1, so that a white solid of X2S(2-Me) was obtained. The white solid was dissolved in pure water and stored as a 1-mM X2S(2-Me) solution for use in the Examples below. X2S(2-M) thus obtained was subjected to MS spectrometry, and a result thereof is shown in Table 1.

Example 13

Evaluation of Excitation Spectrum and Fluorescence Spectrum of Xanthone Fluorescent Molecule X2S, X2S(3), X2S(4), X2S(5), 3,6-X2S(2), and X2S(2-Me) were respectively mixed with cacodylate buffer solutions (sodium cacodylate: 10 mM, pH 7.0; NaCl: 100 mM) each at 10 µM, so that solutions of the respective compounds were obtained.

Figure 19:
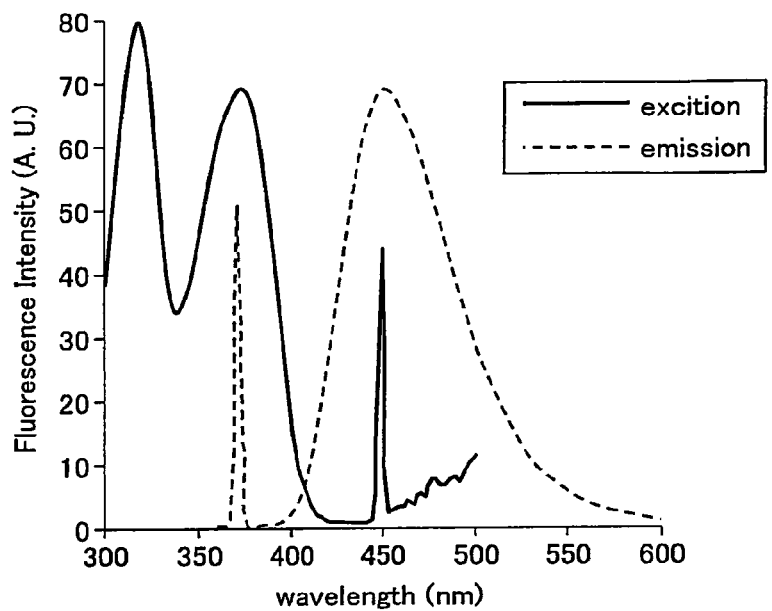
FIG. 19
FIG. 19 is a view illustrating a relationship between an excitation spectrum and a fluorescence spectrum, which relationship was observed when X2S was irradiated with light having an excitation wavelength of 370 nm.

Each of the solutions was irradiated with light, and a fluorescence intensity was measured. The fluorescence intensity was measured with use of a device (product number: RF-5300PC) available from Shimadzu Corporation. A variation in a slit width was set to ±1.5 nm during the excitation, and to ±1.5 nm during the measurement of fluorescence. FIG. 19 is a view illustrating a relationship between an excitation spectrum and a fluorescence spectrum, which relationship was observed when X2S was irradiated with light having an excitation wavelength of 370 nm. In each of FIGS. 19 to 24, the horizontal axis represents the fluorescence wavelength, whereas the vertical axis represents the fluorescence intensity. As shown in FIG. 19, a fluorescence peak of X2S was at 450 nm.

Figure 20:
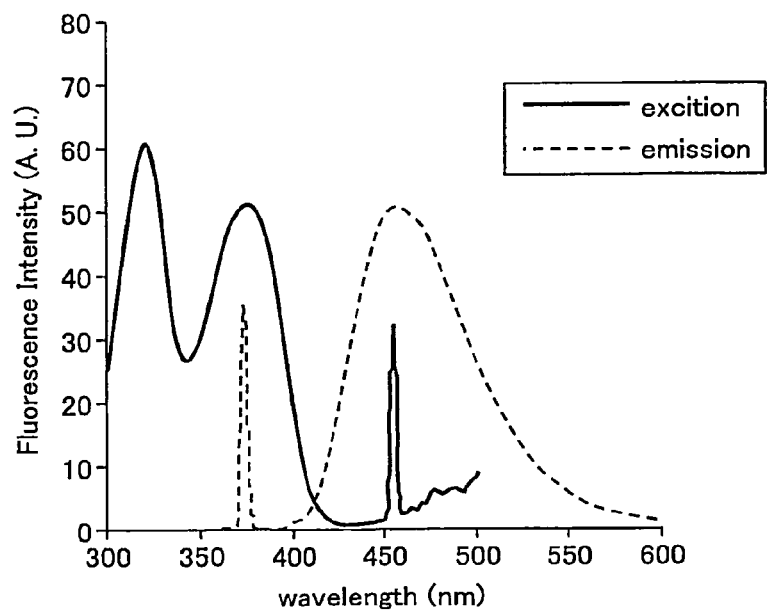
FIG. 20
FIG. 20 is a view illustrating a relationship between an excitation spectrum and a fluorescence spectrum, which relationship was observed when X2S(3) was irradiated with light having an excitation wavelength of 372 nm.

FIG. 20 is a view illustrating a relationship between an excitation spectrum and a fluorescence spectrum, which relationship was observed when X2S(3) was irradiated with light having an excitation wavelength of 372 nm. As shown in FIG. 20, a fluorescence peak of X2S(3) was at 456 nm.

Figure 21:
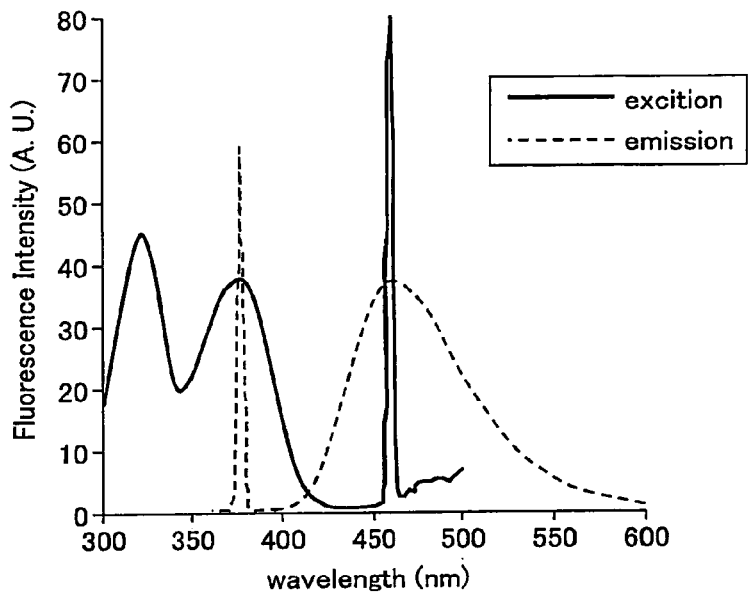
FIG. 21
FIG. 21 is a view illustrating a relationship between an excitation spectrum and a fluorescence spectrum, which relationship was observed when X2S(4) was irradiated with light having an excitation wavelength of 375 nm.

FIG. 21 is a view illustrating a relationship between an excitation spectrum and a fluorescence spectrum, which relationship was observed when X2S(4) was irradiated with light having an excitation wavelength of 375 nm. As shown in FIG. 21, a fluorescence peak of X2S(4) was at 460 nm.

Figure 22:
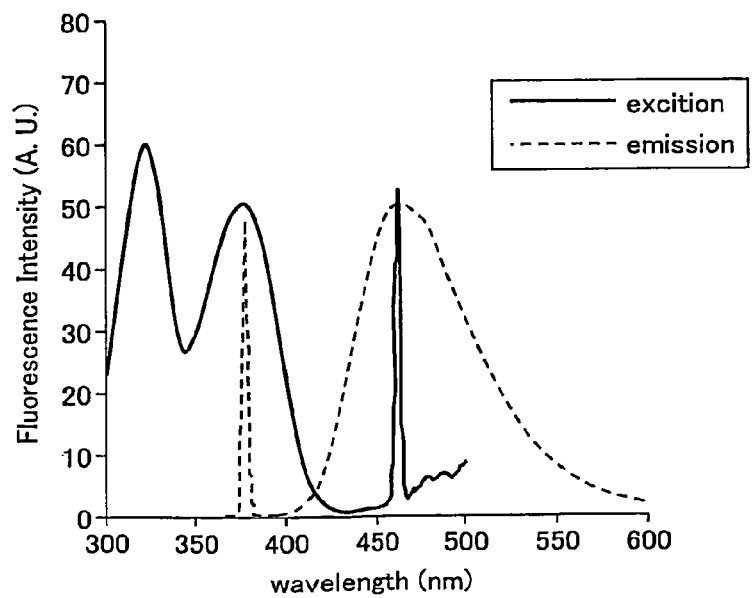
FIG. 22
FIG. 22 is a view illustrating a relationship between an excitation spectrum and a fluorescence spectrum, which relationship was observed when X2S(5) was irradiated with light having an excitation wavelength of 376 nm.

FIG. 22 is a view illustrating a relationship between an excitation spectrum and a fluorescence spectrum, which relationship was observed when X2S(5) was irradiated with light having an excitation wavelength of 376 nm. As shown in FIG. 22, a fluorescence peak of X2S(5) was at 462 nm.

Figure 23:
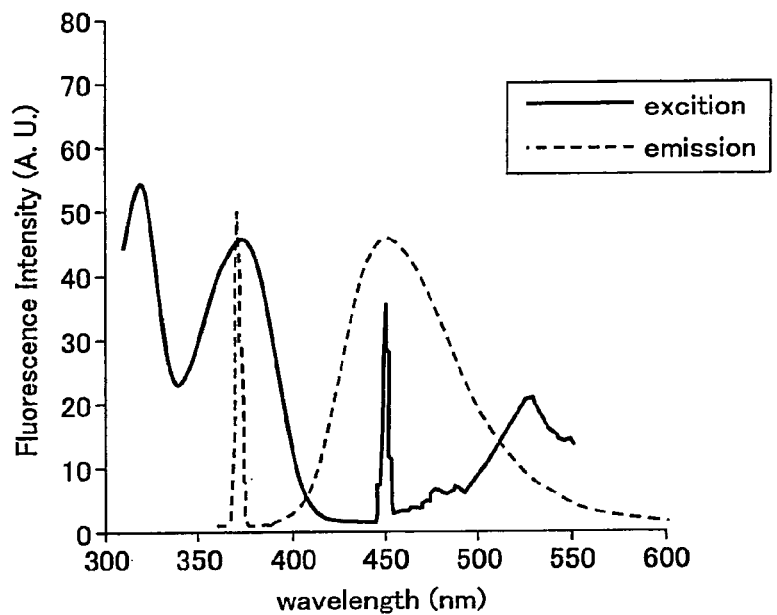
FIG. 23

FIG. 23 is a view illustrating a relationship between an excitation spectrum and a fluorescence spectrum, which relationship was observed when X2S(2-Me) was irradiated with light having an excitation wavelength of 370 nm. As shown in FIG. 23, a fluorescence peak of X2S(2-Me) was at 450 nm.

Figure 24:
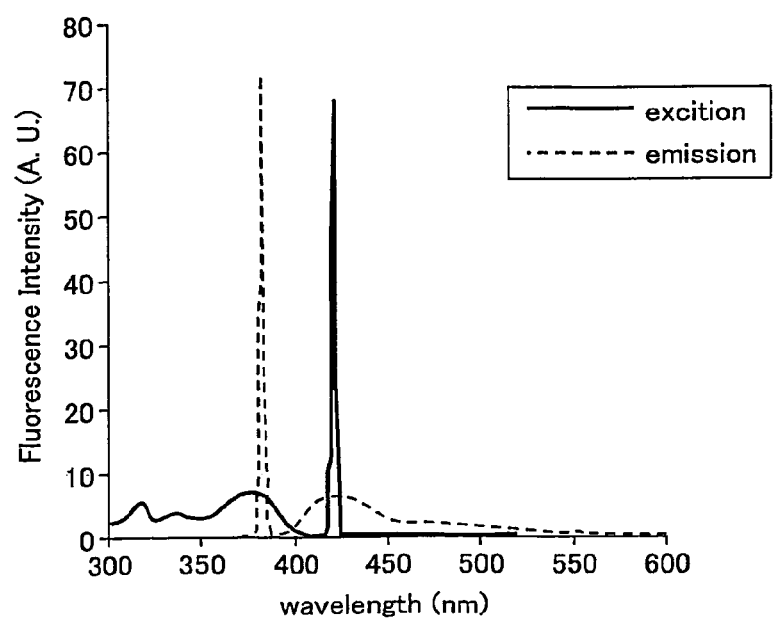
FIG. 24

FIG. 24 is a view illustrating a relationship between an excitation spectrum and a fluorescence spectrum, which relationship was observed when 3,6-X2S(2) was irradiated with light having an excitation wavelength of 322 nm. As shown in FIG. 23, a fluorescence peak of 3,6-X2S(2) was at 373 nm.

Example 14

Fluorescence Titration Experiment Using Double Strand RNA

In this example, the compounds, X2S, X2S(3), X2S(4), X2S(5), X2S(2-Me), and 3,6-X2S(2), were respectively caused to bind to double strand RNAs. Then, changes in fluorescence intensities were observed.

Firstly, X2S, X2S(3), X2S(4), X2S(5), X2S(2-Me), and 3,6-X2S(2) were respectively mixed with cacodylate buffer solutions (sodium cacodylate: 10 mM, pH 7.0; NaCl: 100 mM) each at 1.0 µM, so that solutions of the respective compounds were obtained.

As the double strand RNA, an RNA as in FIG. 2 having N representing no base was used. Specifically, an RNA formed by hybridization of an RNA having the base sequence shown in SEQ ID NO: 1 with an RNA having the base sequence shown in SEQ ID NO: 3 was used. The RNA was added to each of the solutions of the above compositions in steps at 0.0 µM, 0.2 µM, 0.4 µM, 0.8 µM, and 1.0 µM.

Each of the solutions to which the RNAs were added was irradiated with light, and a fluorescence intensity was measured. A device used for measuring the fluorescence intensity was the same as that used in Example 13. A variation in a slit width was set to ±3.0 nm during the excitation, and to ±3.0 nm during the measurement of fluorescence. Results of the measurements are shown in FIGS. 25 to 32.

Figure 25:
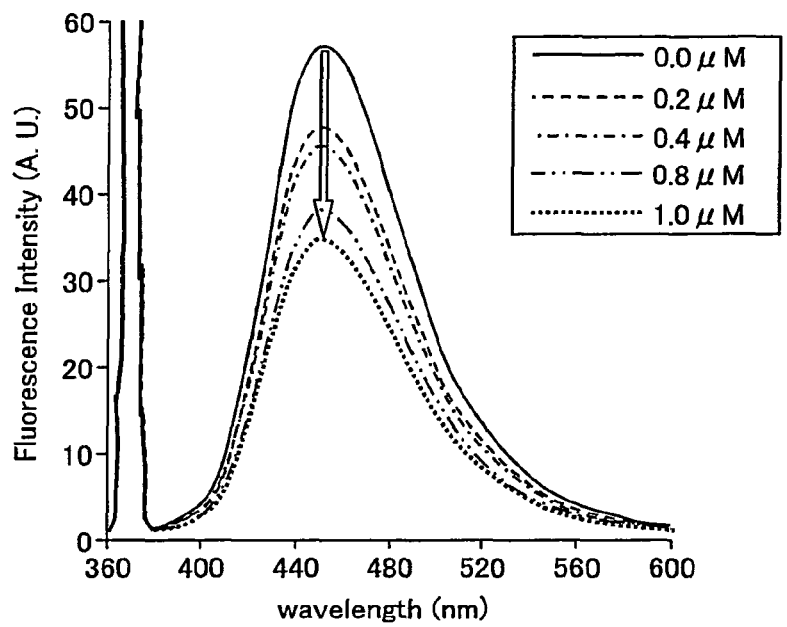
FIG. 25

FIG. 25 is a view illustrating a relationship between a concentration of the RNA and a fluorescence intensity of X2S, which relationship was observed when X2S was irradiated with light having an excitation wavelength of 370 nm.

Figure 26:
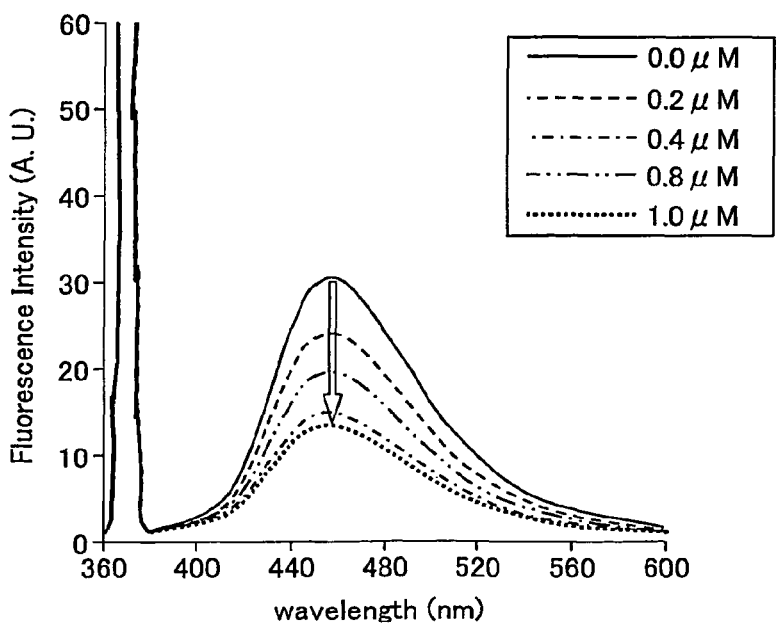
FIG. 26

FIG. 26 is a view illustrating a relationship between a concentration of the RNA and a fluorescence intensity of X2S(3), which relationship was observed when X2S(3) was irradiated with light having an excitation wavelength of 372 nm.

Figure 27:
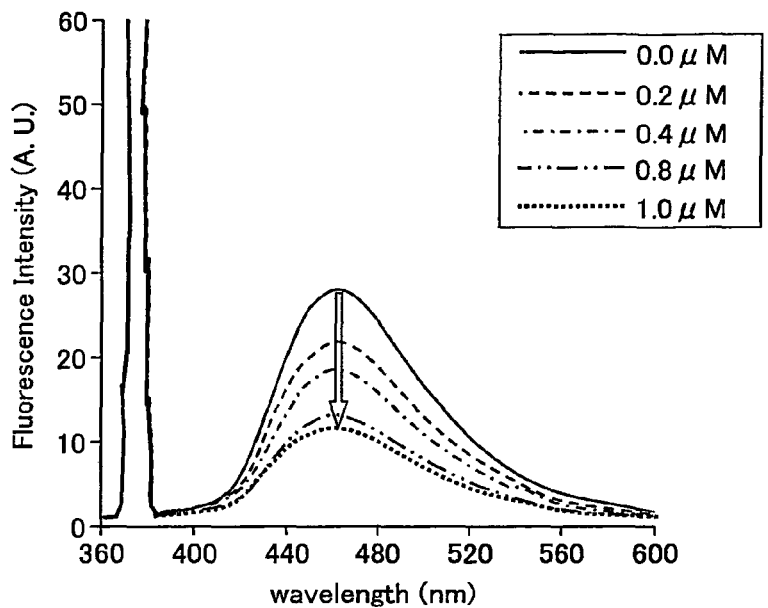
FIG. 27

FIG. 27 is a view illustrating a relationship between a concentration of the RNA and a fluorescence intensity of X2S(4), which relationship was observed when X2S(4) was irradiated with light having an excitation wavelength of 375 nm.

Figure 28:
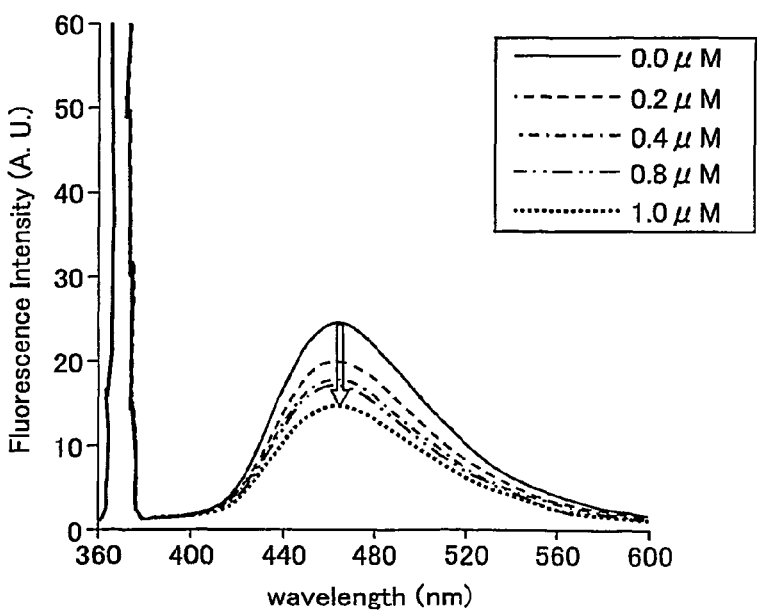
FIG. 28

FIG. 28 is a view illustrating a relationship between a concentration of the RNA and a fluorescence intensity of X2S(5), which relationship was observed when X2S(5) was irradiated with light having an excitation wavelength of 376 nm.

Figure 29:
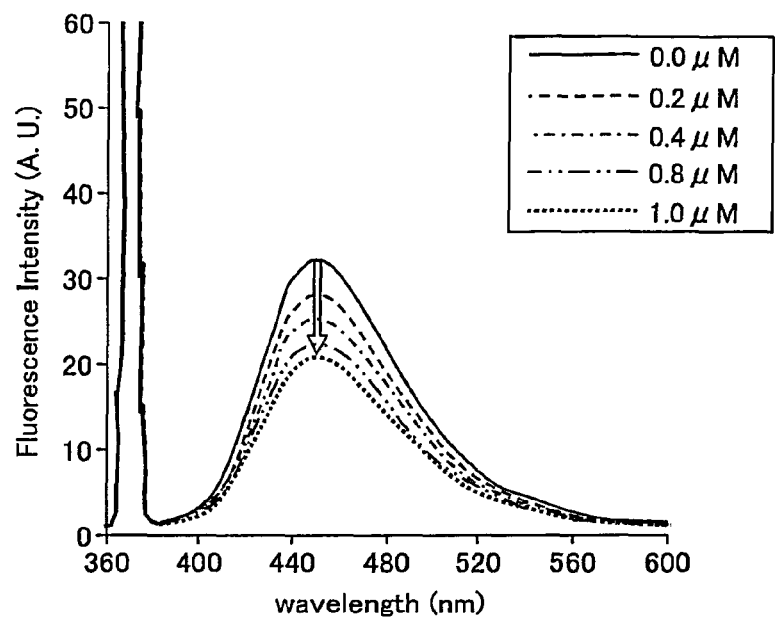
FIG. 29

FIG. 29 is a view illustrating a relationship between a concentration of the RNA and a fluorescence intensity of X2S(2-Me), which relationship was observed when X2S(2-Me) was irradiated with light having an excitation wavelength of 370 nm.

Figure 30:
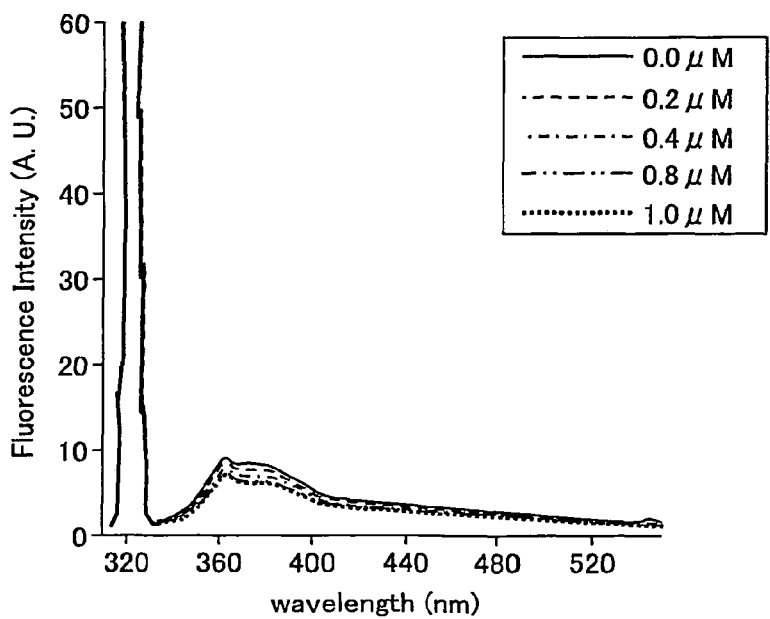
FIG. 30

FIG. 30 is a view illustrating a relationship between a concentration of the RNA and a fluorescence intensity of 3,6-X2S(2), which relationship was observed when 3,6-X2S(2) was irradiated with light having an excitation wavelength of 322 nm.

In each of FIGS. 25 to 30, the horizontal axis represents the fluorescence wavelength, whereas the vertical axis represents the fluorescence intensity. The direction of the arrow in each of FIGS. 25 to 30 shows an increasing order of concentrations of the RNA at which the respective curved lines were obtained. That is, the curved line at the top shows a result obtained at a concentration of 0.0 µM of the RNA, and the curved line at the bottom shows a result obtained at a concentration of 1.0 µM of the RNA.

Figure 31:
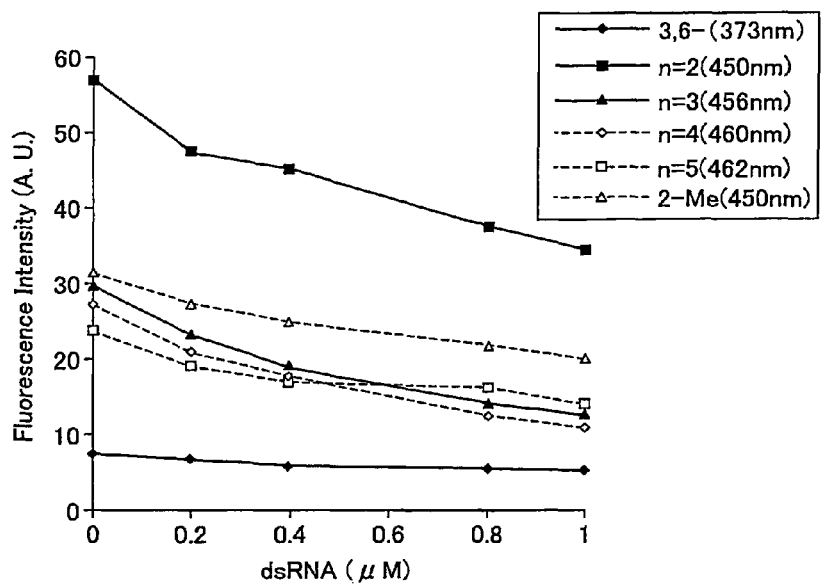
FIG. 31
Figure 32:
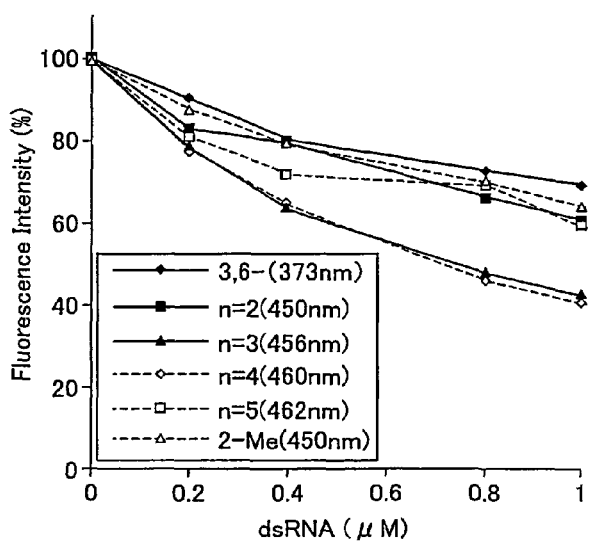
FIG. 32

FIG. 31 is a graph illustrating a relationship between a concentration of the double strand RNA added and a fluorescence intensity of each compound. Further, FIG. 31 is also a view plotting the fluorescence intensities of the respective fluorescence peaks shown in the results illustrated in FIGS. 25 to 30. FIG. 32 is a view plotting residual fluorescence intensities (%) observed at each concentration of the double strand RNA added, based on the results shown in FIGS. 25 to 30.

Note that the "residual fluorescence intensity (%)" herein is represented in percentage representing a ratio of (i) a fluorescence intensity (B) observed at each concentration of a double strand RNA added with respect to (ii) a fluorescence intensity (A) of a fluorescence peak observed at a concentration of 0.0 µM of the RNA.

In each of FIGS. 31 and 32, the horizontal axis represents the concentration of the RNA. In FIG. 31, the vertical axis represents the fluorescence intensity. In FIG. 32, the vertical axis represents the residual fluorescence intensity (%).

FIGS. 25 to 32 show that the fluorescence intensity was reduced as the concentration of the RNA increased. This verifies that, once each compound used in this Example binds to an RNA, its fluorescence intensity is reduced. A degree of the reduction was different between the compounds. As is clear from FIG. 32, X2S(3) and X2S(4) showed particularly high reduction rates.

Example 15

Fluorescence Titration Experiment Using RRE

In this example, the compounds, X2S, X2S(3), X2S(4), X2S(5), X2S(2-Me), and 3,6-X2S(2), were respectively caused to bind to RREs. Then, changes in fluorescence intensities were observed.

Firstly, X2S, X2S(3), X2S(4), X2S(5), X2S(2-Me), and 3,6-X2S(2) were respectively mixed with cacodylate buffer solutions (sodium cacodylate: 10 mM, pH 7.0; NaCl: 100 mM) each at 1.0 µM, so that solutions of the respective compounds were obtained. RRE used in this Example was the same as that used in Example 4. RRE was added to each of the solutions of the respective compounds in steps at 0.0 µM, 0.2 µM, 0.4 µM, 0.8 µM, and 1.0 µM.

Each of the solutions to which RRE was added was irradiated with light, and a fluorescence intensity was measured. A device used for measuring the fluorescence intensity was the same as that used in Example 13. A variation in a slit width was also the same as that in Example 14. Results of the measurements are shown in FIGS. 33 to 42.

Figure 33:
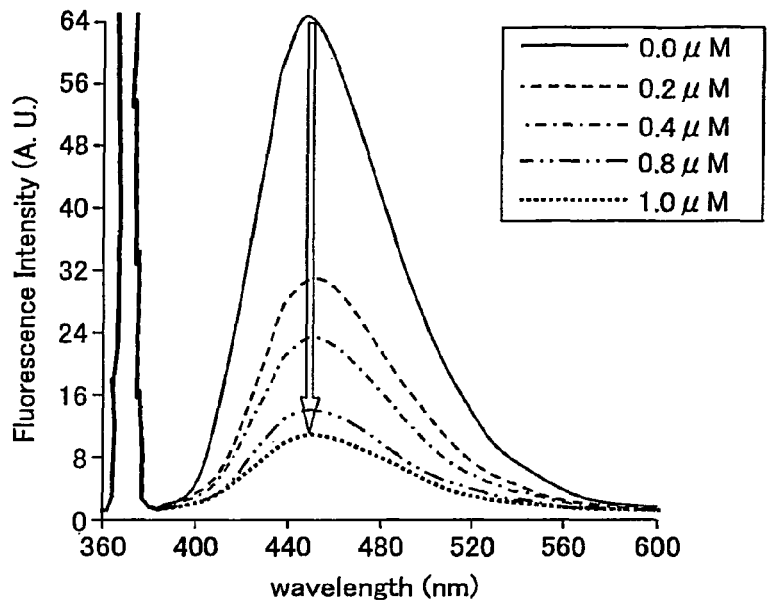
FIG. 33

FIG. 33 is a view illustrating a relationship between a concentration of RRE and a fluorescence intensity of X2S, which relationship was observed when X2S was irradiated with light having an excitation wavelength of 370 nm.

Figure 34:
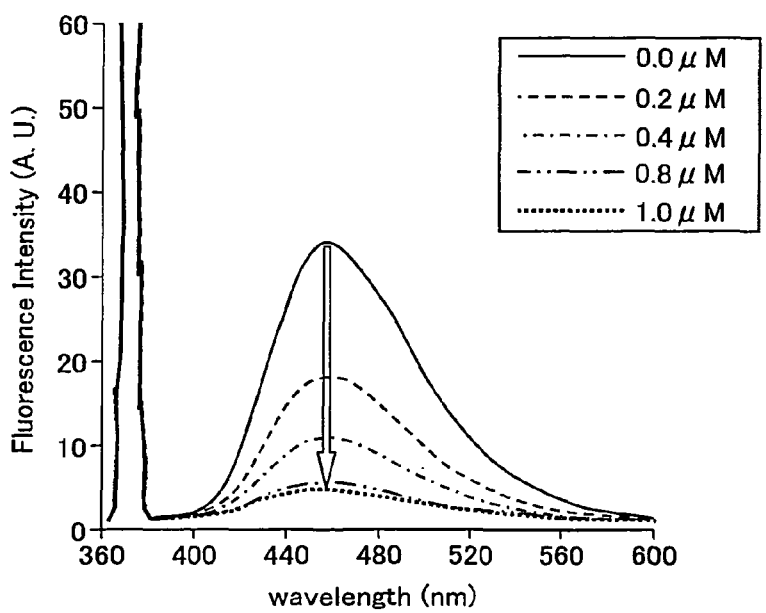
FIG. 34

FIG. 34 is a view illustrating a relationship between a concentration of RRE and a fluorescence intensity of X2S(3), which relationship was observed when X2S(3) was irradiated with light having an excitation wavelength of 372 nm.

Figure 35:
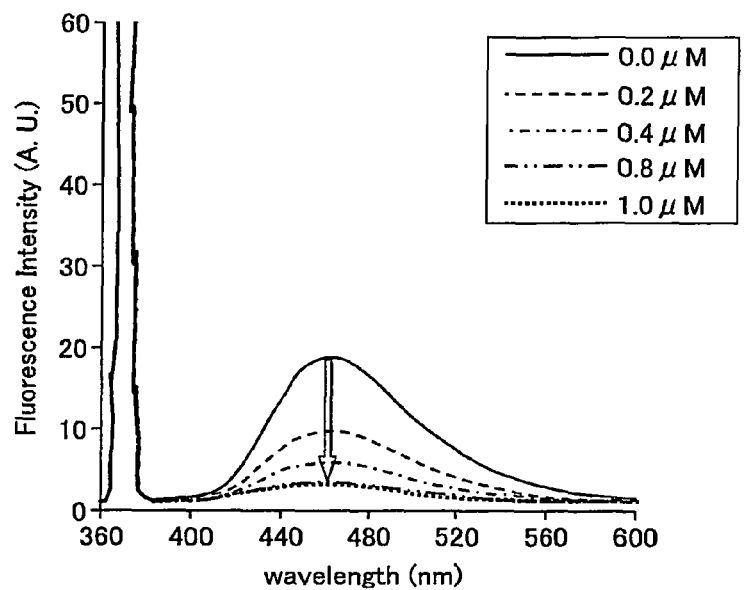
FIG. 35

FIG. 35 is a view illustrating a relationship between a concentration of RRE and a fluorescence intensity of X2S(4), which relationship was observed when X2S(4) was irradiated with light having an excitation wavelength of 375 nm.

Figure 36:
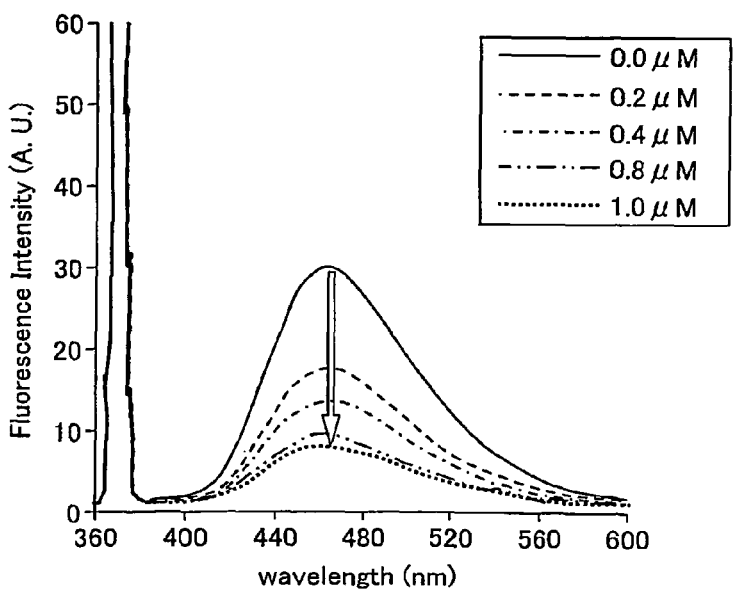
FIG. 36

FIG. 36 is a view illustrating a relationship between a concentration of RRE and a fluorescence intensity of X2S(5), which relationship was observed when X2S(5) was irradiated with light having an excitation wavelength of 376 nm.

Figure 37:
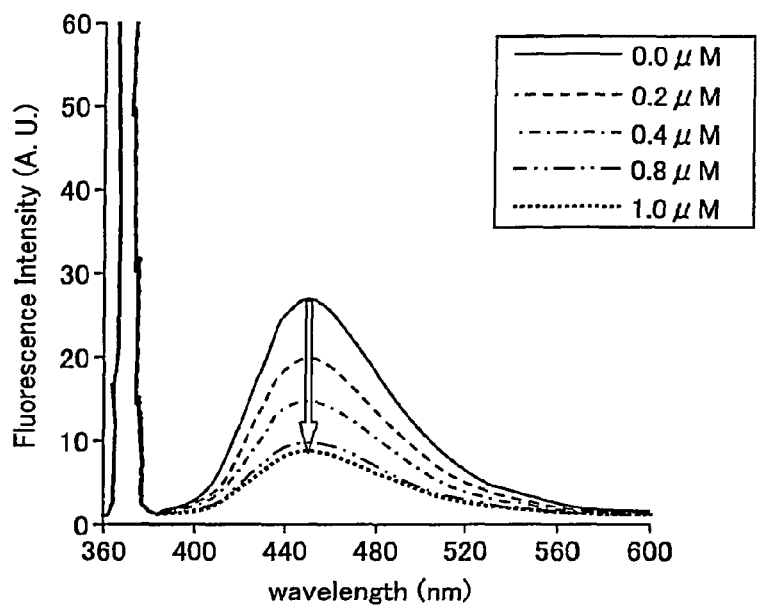
FIG. 37

FIG. 37 is a view illustrating a relationship between a concentration of RRE and a fluorescence intensity of X2S(2-Me), which relationship was observed when X2S(2-Me) was irradiated with light having an excitation wavelength of 370 nm.

Figure 38:
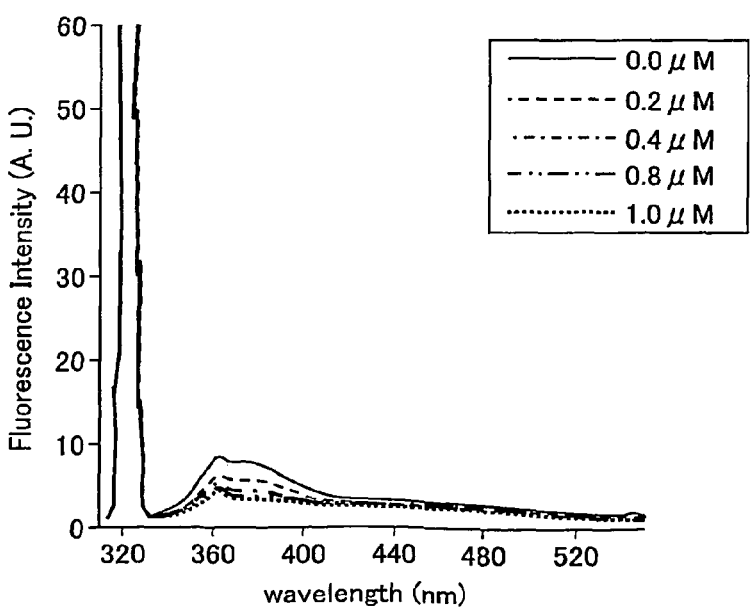
FIG. 38

FIG. 38 is a view illustrating a relationship between a concentration of RRE and a fluorescence intensity of 3,6-X2S(2), which relationship was observed when 3,6-X2S(2) was irradiated with light having an excitation wavelength of 322 nm.

In each of FIGS. 33 to 38, the horizontal axis represents the fluorescence wavelength, whereas the vertical axis represents the fluorescence intensity. The direction of the arrow in each of FIGS. 33 to 38 shows an increasing order of concentrations of RRE at which the respective curved lines were obtained. That is, the curved line at the top shows a result obtained at a concentration of 0.0 µM of RRE, and the curved line at the bottom shows a result obtained at a concentration of 1.0 µM of RRE.

Figure 39:
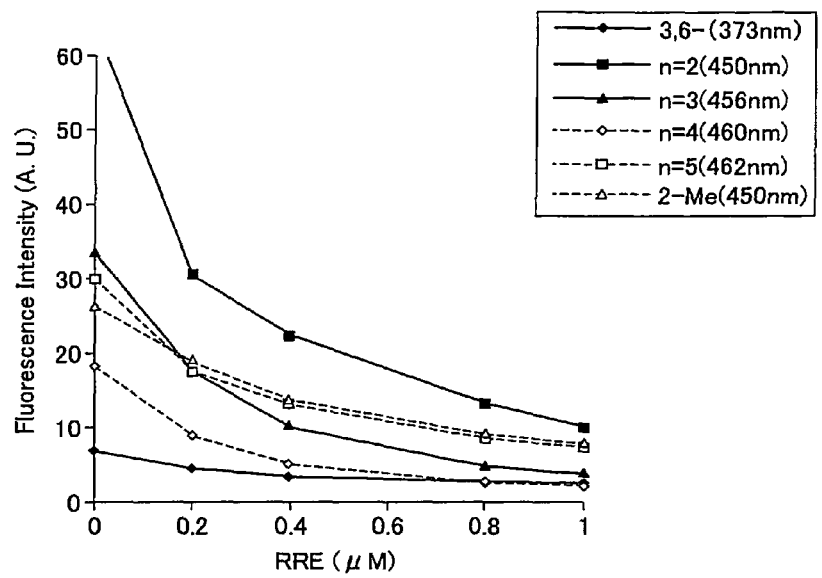
FIG. 39
Figure 40:
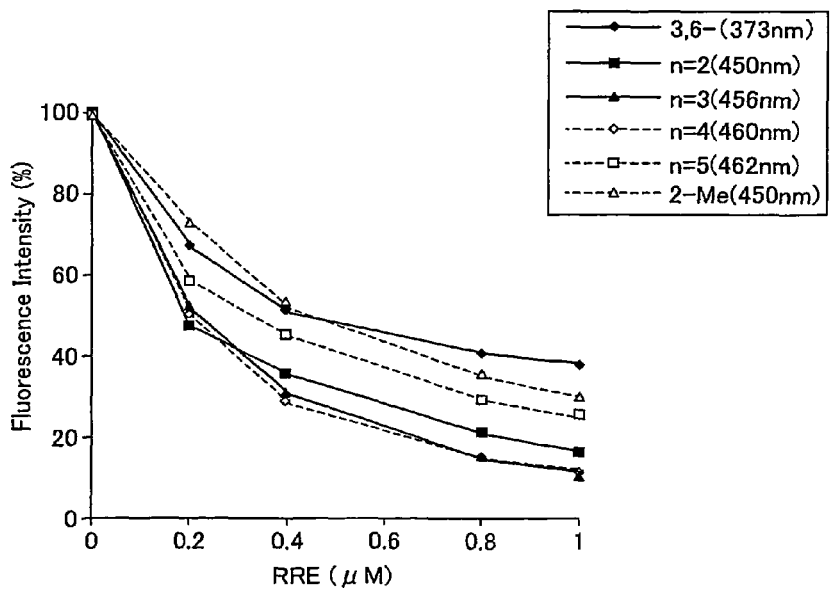
FIG. 40

FIG. 39 is a graph illustrating a relationship between a concentration of RRE added and a fluorescence intensity of each compound. Further, FIG. 39 is also a view plotting the fluorescence intensities of the respective fluorescence peaks shown in the results illustrated in FIGS. 33 to 38. FIG. 40 is a view plotting residual fluorescence intensities (%) which were obtained based on the results shown in FIGS. 33 to 38, assuming that the fluorescence intensities of the respective fluorescence peaks observed at a concentration of 0.0 µM of RRE were 100%. In each of FIGS. 39 and 40, the horizontal axis represents the concentration of the RNA. In FIG. 39, the vertical axis represents the fluorescence intensity. In FIG. 40, the vertical axis represents the residual fluorescence intensity (%).

Figure 41:
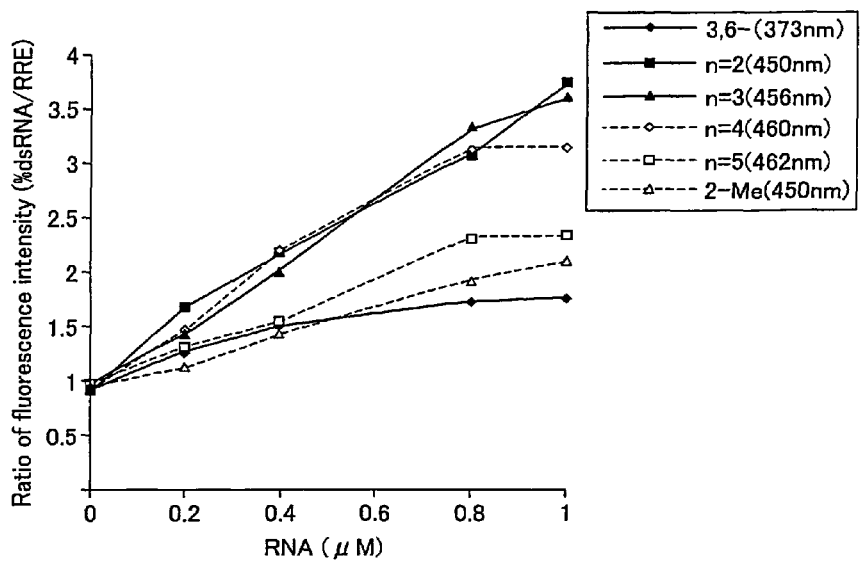
FIG. 41
Figure 42:
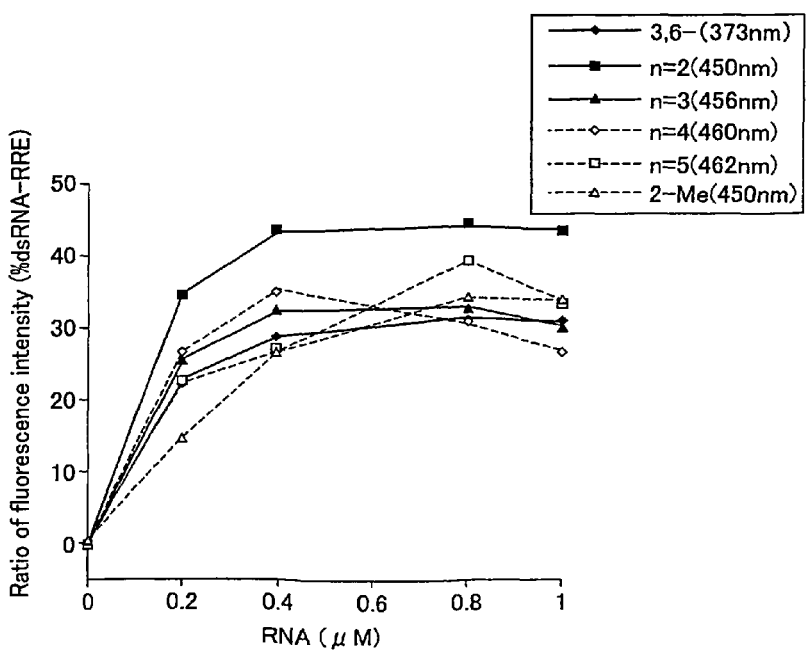
FIG. 42

Each of FIGS. 41 and 42 shows a result of evaluation of a difference between (i) the fluorescence intensity observed in the measurement with use of RRE and (ii) the fluorescence intensity observed in the measurement with use of the double strand RNA which was used in Example 14. FIG. 41 is a view plotting values obtained by dividing (i) the residual fluorescence intensities (%) obtained in the case involving use of the double strand RNA by (ii) the residual fluorescence intensities (%) obtained in the case involving use of RRE. That is, FIG. 41 is a view plotting values obtained by dividing (i) the residual fluorescence intensity (%) shown in FIG. 32 by (ii) the residual fluorescence intensities (%) shown in FIG. 40. FIG. 42 is a view plotting values obtained by subtracting (i) the residual fluorescence intensities (%) obtained in the case involving use of RRE from (ii) the residual fluorescence intensities (%) obtained in the case involving use of the double strand RNA. That is, FIG. 42 is a view plotting values obtained by subtracting (i) the residual fluorescence intensities (%) shown in FIG. 40 from (ii) the residual fluorescence intensities (%) shown in FIG. 32.

FIGS. 33 to 40 show that, also in the case involving use of RRE, the fluorescence intensity was reduced as the concentration of RRE increased. This verifies that, once each compound used in this Example binds to RRE, its fluorescence intensity is reduced. A degree of the reduction was different between the compounds. As is clear from FIG. 40, X2S, X2S(3), and X2S(4) tended to have particularly high reduction rates. Further, FIGS. 41 and 42 show that: (i) a reduction in the fluorescence intensity was smaller in the case involving use of the double strand RNA than in the case involving use of RRE; and (ii) a difference in quenching efficiency between the case involving use of RRE and the case involving use of the double strand RNA was greatest in the cases where X2S, X2S(3), and X2S(4) were used. The difference in quenching efficiency was saturated at the point that RRE or the double strand RNA was added at approximately 0.4 µM.

Example 16

Displacement Assay Using Rev Peptide After Formation of Complex with RRE

In this Example, a binding affinity between a test substance and RRE was evaluated, with use of the compounds, X2S, X2S(3), X2S(4), X2S(5), X2S(2-Me), and 3,6-X2S(2). As the test substance, Rev protein used in Example 5 was used.

Firstly, in the same manner as in Example 3, the above compounds and RREs were respectively dissolved in cacodylate buffer solutions (sodium cacodylate: 10 mM pH 7.0, NaCl: 100 mM) each at 2 µM, so that an X2S-RRE solution, an X2S(3)-RRE solution, an X2S(4)-RRE solution, an X2S(5)-RRE solution, an X2S(2-Me)-RRE solution, and a 3,6-X2S(2)-RRE solution were prepared.

To each of these solutions, Rev protein was added in stages at 0 µM, 0.4 µM, 0.8 µM, 1.2 µM, 1.6 µM, 2.0 µM, 2.4 µM, 2.8 µM, 3.2 µM, 3.6 µM, and 4.0 µM. Further, a fluorescence intensity was measured at each concentration. The fluorescence intensity was measured in the same manner as that described in Example 14.

Figure 43:
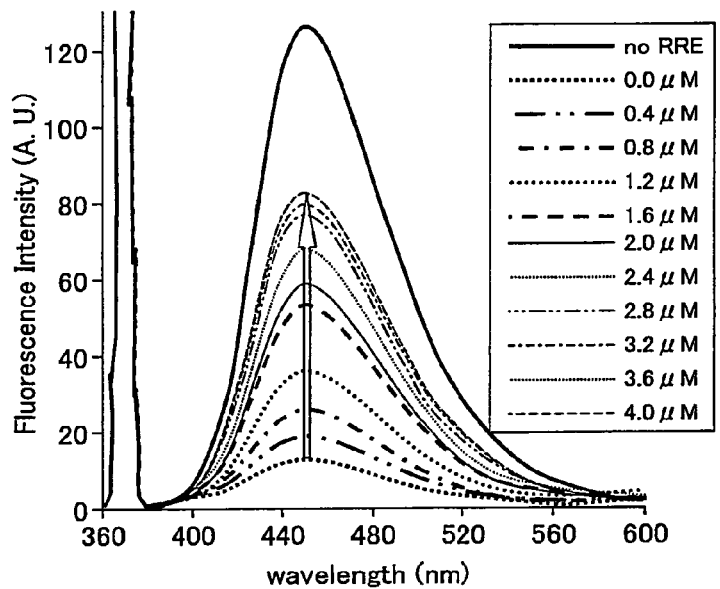
FIG. 43
Figure 44:
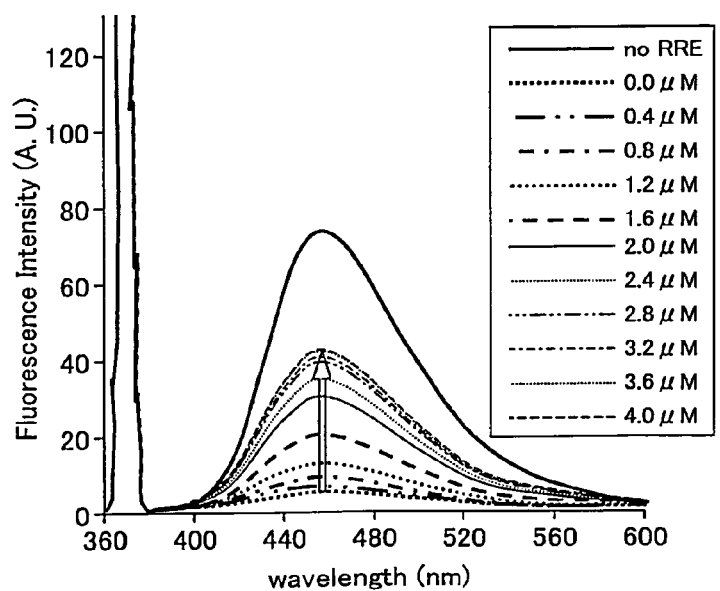
FIG. 44
Figure 45:
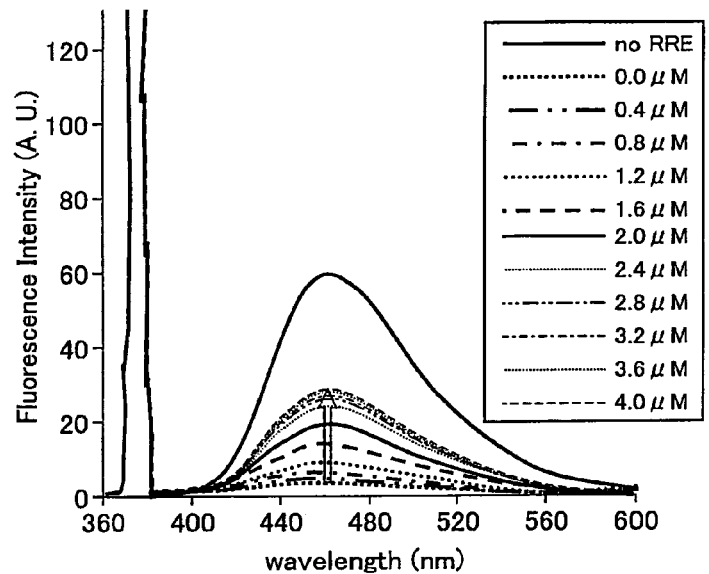
FIG. 45
Figure 46:
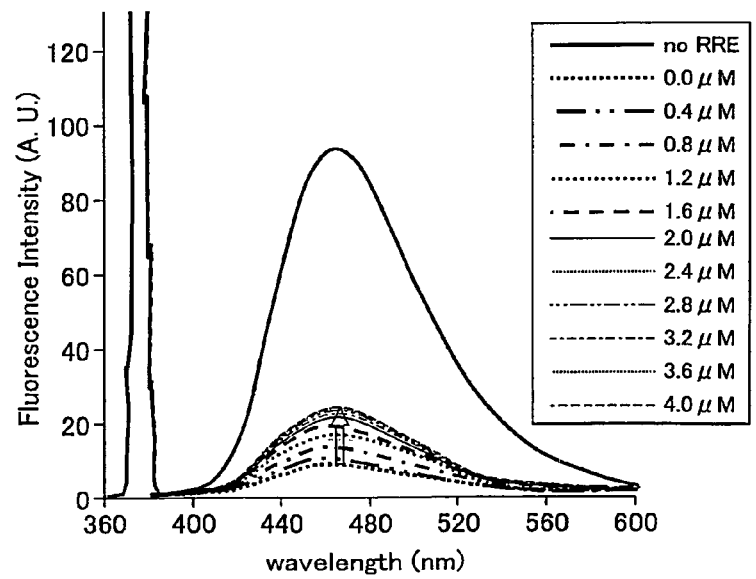
FIG. 46
Figure 47:
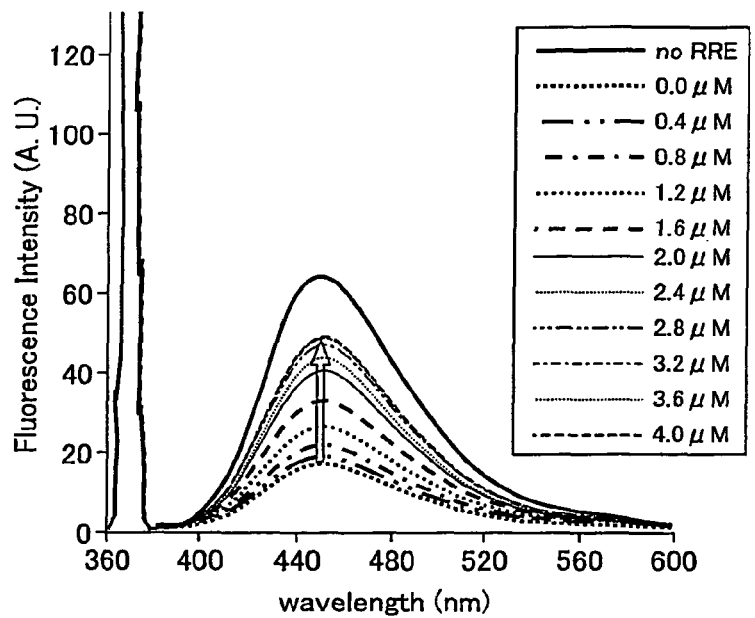
FIG. 47
Figure 48:
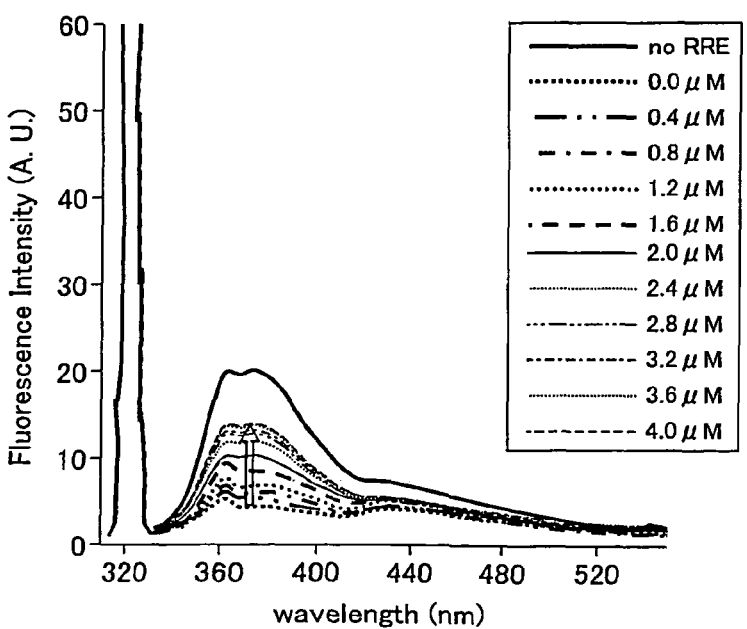
FIG. 48

Results of the measurements are shown in FIGS. 43 to 50. Each of FIGS. 43 to 48 is a view illustrating a result of the measurement of a binding affinity between Rev protein and RRE. FIG. 43 shows a result obtained in the case involving use of X2S; FIG. 44 shows a result obtained in the case involving use of X2S(3); FIG. 45 shows a result obtained in the case involving use of X2S(4); FIG. 46 shows a result obtained in the case involving use of X2S(5); FIG. 47 shows a result obtained in the case involving use of X2S(2-Me); and FIG. 48 shows a result in the case involving 3,6-X2S(2). In each of FIGS. 43 to 48, the horizontal axis represents the fluorescence wavelength, whereas the vertical axis represents the fluorescence intensity. In each of FIGS. 43 to 48, the curved line at the top shows a fluorescence intensity detected in the absence of RRE, and the curved line at the bottom shows a fluorescence intensity detected in the presence of RRE and a corresponding one of the compounds but in the absence of the test substance. Further, along the direction of the arrow extending from the curved line at the bottom, the curved lines, showing the respective results, are arranged in order of increasing amount of the test substance which was added.

Figure 49:
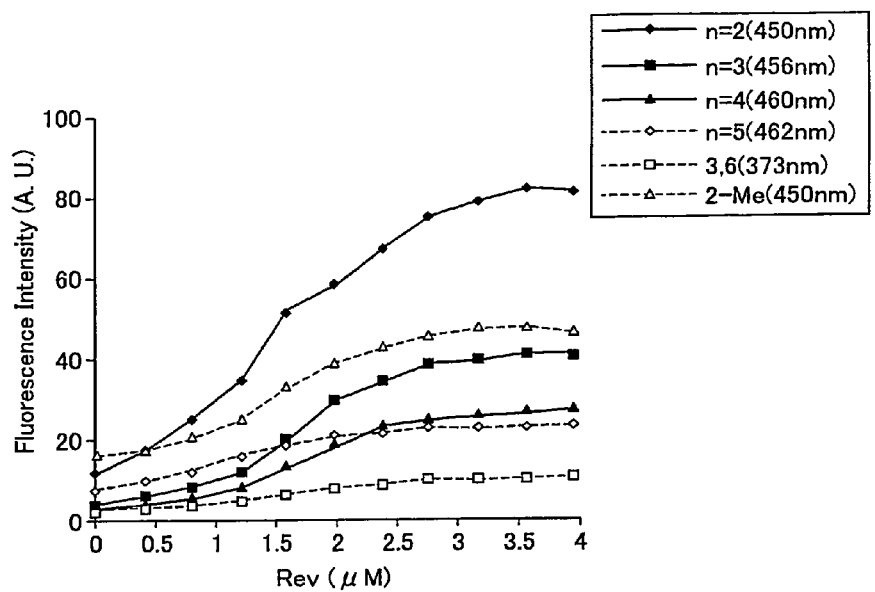
FIG. 49
Figure 50:
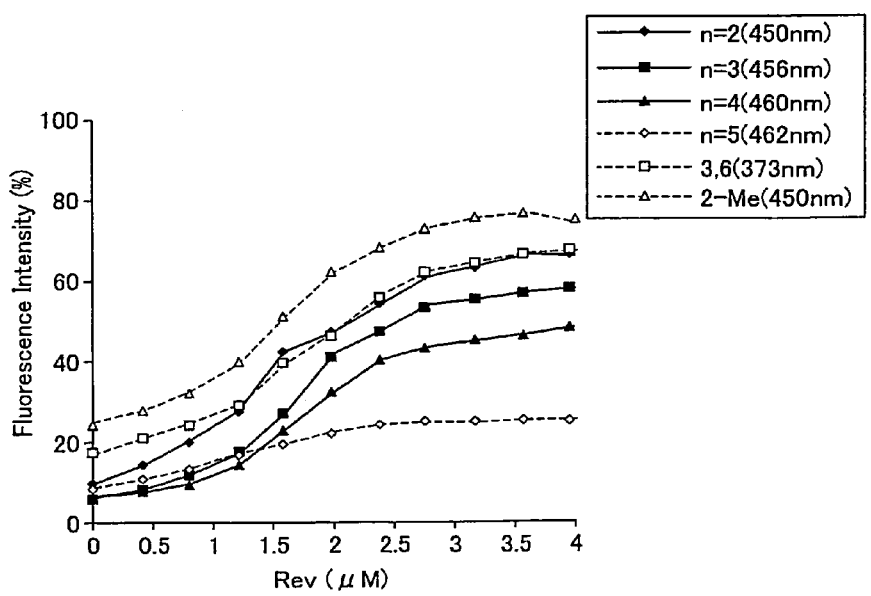
FIG. 50

FIG. 49 is a view illustrating a relationship between an amount of Rev added and a fluorescence intensity, in connection with X2S, X2S(3), X2S(4), X2S(5), X2S(2-Me), and 3,6-X2S(2). Further, FIG. 49 is also a view plotting, based on the results illustrated in FIGS. 43 to 48, the fluorescence intensities detected at the fluorescence wavelength at which the respective fluorescence peaks were observed. FIG. 50 is a graph illustrating a relationship between an amount of Rev added and a recovery rate of the fluorescence intensity. In FIG. 49, the vertical axis represents the fluorescence intensity. In FIG. 50, the vertical axis represents the recovery rate of the fluorescence intensity. In each of FIGS. 49 and 50, the horizontal axis represents the amount of Rev added. That is, each of FIGS. 49 and 50 reflects amounts of the above compounds liberated from RREs due to the addition of Rev.

The recovery rate of the fluorescence intensity was obtained by dividing (i) a maximum value of the fluorescence intensity detected at each Rev concentration ranging from 0 µM to 4.0 µM in each of FIGS. 43 to 48 by (ii) a maximum value of the fluorescence intensity of the curved line at the top in each of FIGS. 43 to 48.

FIGS. 43 to 50 verify that the addition of Rev protein increased the fluorescence intensity. This shows that, as Rev protein increased, Rev protein bound to RRE in place of each of the above compounds which had bound to RRE, and consequently said each of the compounds was liberated from RRE. This shows that Rev protein has a significantly high binding affinity with respect to RRE, and further shows that a binding affinity of Rev protein with respect to RRE is measurable with use of the above compounds.

X2S exhibited a high fluorescence intensity, and also showed a good recovery rate of the fluorescence intensity. Although X2S(2-Me) exhibited a fluorescence intensity lower than that of X2S, it showed a highest recovery rate of the fluorescence intensity. Although 3,6-X2S(2) exhibited a low fluorescence intensity, it showed a recovery rate of the fluorescence intensity almost equal to that of X2S, which was good.

Example 17

Evaluation of Excitation Spectrum and Fluorescence Spectrum of Pyrene Fluorescent Molecule 1-Pyrenemethanamide, hydrochloride was added to a cacodylate buffer solution (sodium cacodylate: 10 mM, pH 7.0; NaCl: 100 mM) at 10 µM, so that a solution thereof was obtained. The solution was irradiated with light having an excitation wavelength of 340 nm, and a fluorescence intensity was measured. A device used for measuring the fluorescence intensity and a slit width were the same as those in Example 13.

Figure 51:
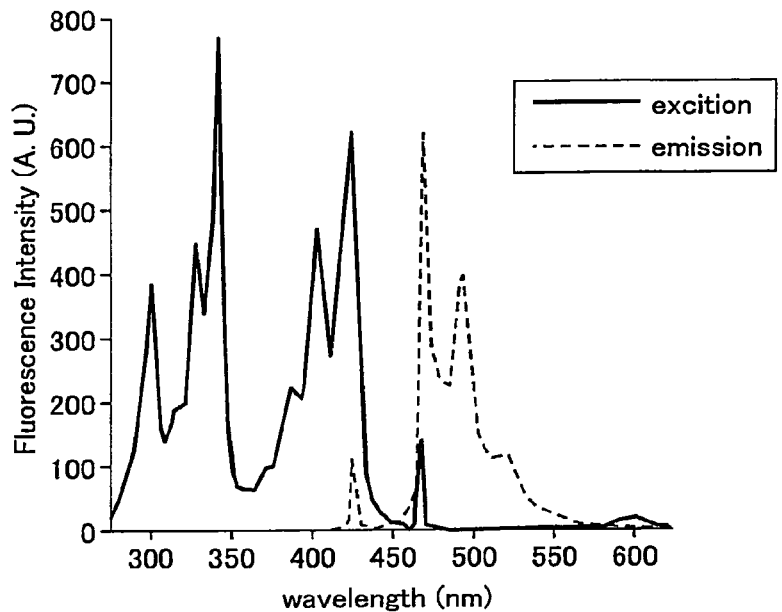
FIG. 51

FIG. 51 is a view illustrating a relationship between an excitation spectrum and a fluorescence spectrum, in connection with 1-Pyrenemethanamide, hydrochloride. The horizontal axis represents the fluorescence wavelength, whereas the vertical axis represents the fluorescence intensity. As shown in FIG. 51, a fluorescence peak was at 375 nm.

Example 18

Fluorescence Titration Experiment Using Double Strand RNA and RRE

In this Example, 1-Pyrenemethanamide, hydrochloride was caused to bind to a double strand RNA or RRE. Then, a change in a fluorescence intensity was observed.

As well as in Example 14, the double strand RNA used in this Example was an RNA formed by hybridization of an RNA having the base sequence shown in SEQ ID NO: 1 with an RNA having the base sequence shown in SEQ ID NO: 3. RRE used in this Example was the same as that used in Example 4.

The double strand RNA or RRE was added in steps to the solution prepared in Example 17 at 0.0 μM, 0.2 μM, 0.4 μM, 0.8 μM, and 1.0 μM.

Figure 52:
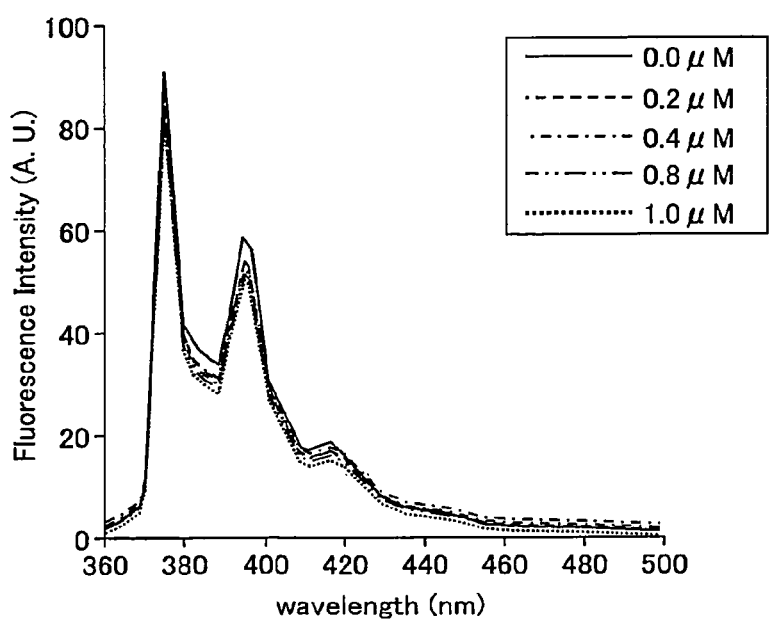
FIG. 52
Figure 53:
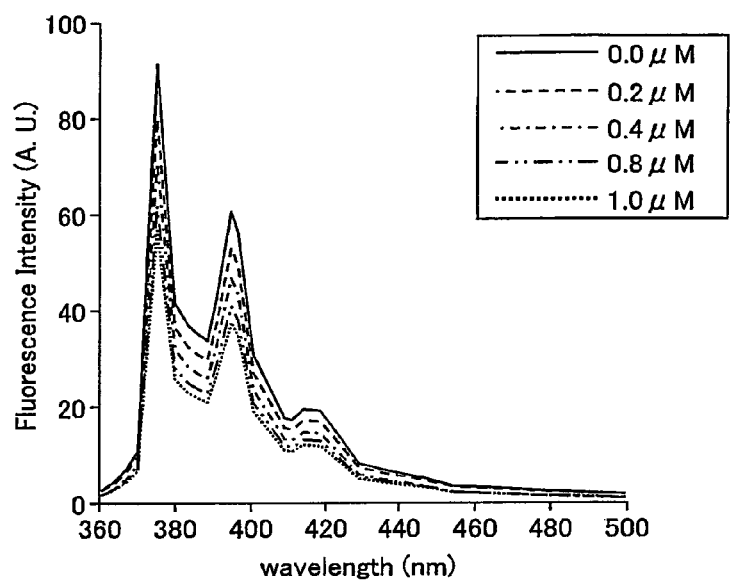
FIG. 53
Figure 54:
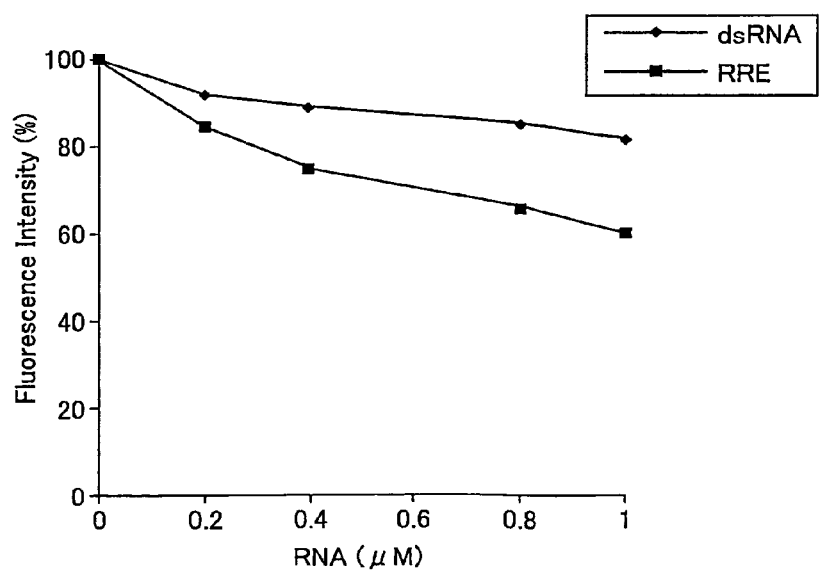
FIG. 54

The solution to which the RNA was added was irradiated with light having an excitation wavelength of 340 nm, and a fluorescence intensity was measured. A device used for measuring the fluorescence intensity and a variation in a slit width were the same as those in Example 13. Results of the measurements are shown in FIGS. 52 to 54. In each of FIGS. 52 and 53, the horizontal axis represents the fluorescence wavelength, whereas the vertical axis represents the fluorescence intensity.

FIG. 52 is a view illustrating a result of evaluation of binding between 1-Pyrenemethanamide, hydrochloride and the double strand RNA. FIG. 53 is a view illustrating a result of evaluation of binding between 1-Pyrenemethanamide, hydrochloride and RRE. In each of FIGS. 52 and 53, the curved line at the top shows a result obtained at a concentration of 0 μM of the RNA. Further, along a top-to-bottom direction, the curved lines, showing the respective results, are arranged in order of increasing concentration of the RNA. The curved line at the bottom shows a result obtained at a concentration of 1.0 μM of the RNA. FIG. 54 is a view plotting residual fluorescence intensities (%) of 1-Pyrenemethanamide obtained from the fluorescence intensities detected at a fluorescence wavelength of 375 nm and at the different RNA concentrations. In FIG. 54, the horizontal axis represents the concentration of the RNA, whereas the vertical axis represents the residual fluorescence intensity (%).

FIGS. 52 to 54 show that the fluorescence intensity was reduced as the concentration of the RNA increased. This verifies that, once 1-Pyrenemethanamide, hydrochloride binds to an RNA, its fluorescence intensity is reduced. A reduction in the fluorescence intensity was more significant in the case involving use of RRE than in the case involving use of the double strand RNA.

Example 19

Displacement Assay Using Rev Peptide After Formation of Complex with RRE

In this Example, 1-Pyrenemethanamide, hydrochloride was used to measure a binding affinity between a test substance and RRE. As the test substance, Rev protein used in Example 5 was used.

Firstly, in the same manner as in Example 3, 1-Pyrenemethanamide, hydrochloride and RRE were dissolved in a cacodylate buffer solution (sodium cacodylate: 10 mM, pH 7.0; NaCl: 100 mM) each at 2 μM, so that a 1-Pyrenemethanamide, hydrochloride-RRE solution was prepared.

To the solution, Rev protein was added in steps at 0 μM, 0.4 μM, 0.8 μM, 1.2 μM, 1.6 μM, 2.0 μM, 2.4 μM, 2.8 μM, 3.2 μM, 3.6 μM, and 4.0 μM. Further, the solution at each concentration was irradiated with light having an excitation wavelength of 340 nm, and a fluorescence intensity was measured. A device used for measuring a fluorescence intensity and a variation in a slit width were the same as those in Example 13.

Figure 55:
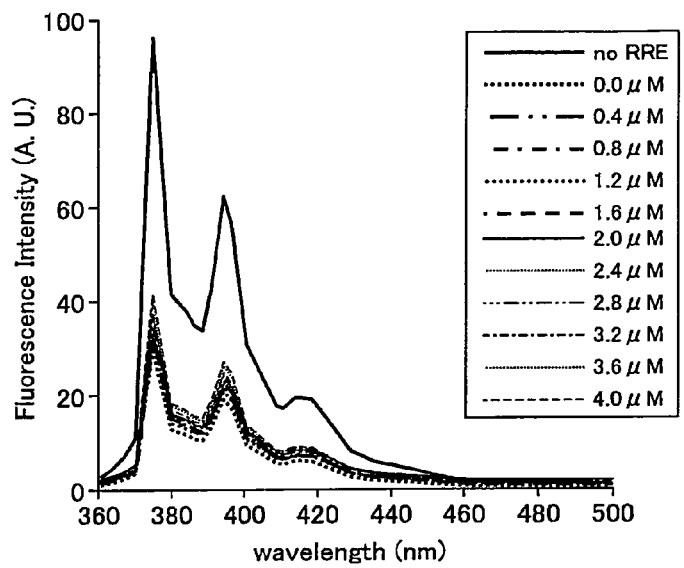
FIG. 55
Figure 56:
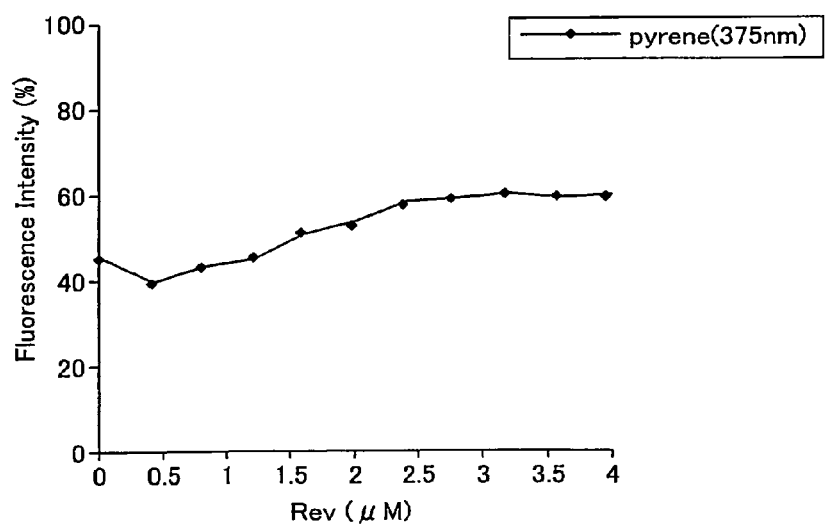
FIG. 56

A result of the measurement is shown in FIGS. 55 and 56. FIG. 55 is a view illustrating a result of the measurement of a binding affinity between Rev protein and RRE. The horizontal axis represents the fluorescence wavelength, whereas the vertical axis represents the fluorescence intensity. The curved line at the top shows a fluorescence intensity detected in the absence of RRE, and the curved line at the bottom shows a fluorescence intensity detected in the presence of RRE and each compound but in the absence of the test substance. Further, along a bottom-to-top direction, the curved lines, showing the respective results, are arranged in order of increasing amount of the test substance which was added.

FIG. 56 is a graph illustrating a relationship between an amount of Rev added and a recovery rate of the fluorescence intensity. The vertical axis represents the recovery rate of the fluorescence intensity, whereas the horizontal axis represents the amount of Rev added. Each recovery rate of the fluorescence intensity was obtained as follows: Each fluorescence intensity detected at a fluorescence wavelength of 340 nm, shown in FIG. 55, is divided by the fluorescence intensity of the curved line at the top detected at a fluorescence wavelength of 340 nm, shown in FIG. 55; and the value thus obtained is multiplied by 100.

FIGS. 55 and 56 show that the addition of Rev protein increased the fluorescence intensity. This shows that, as Rev protein increased, Rev protein bound to RRE in place of 1-Pyrenemethanamide, hydrochloride which had bound to RRE, and consequently each compound was liberated from RRE. Further, the recovery rate of the fluorescence intensity observed here was almost equal to that of X2S. This shows that a binding affinity of Rev protein with respect to RRE is measurable with use of 1-Pyrenemethanamide, hydrochloride.

As described above, a composition of the present invention for measuring a binding affinity between a nucleic acid and a test substance includes an organic fluorescent substance which is capable of binding to an RNA and which emits fluorescence having an intensity greater while the organic fluorescent substance is liberated from an RNA than while the organic fluorescent substance is bound to an RNA. This allows various substances to be examined as a test substance, and enables a highly accurate and easy measurement of a binding affinity between the test substance and a nucleic acid.

Further, the compound of the present invention for measuring a binding affinity between a nucleic acid and a test substance includes a compound represented by the following General Formula (1):

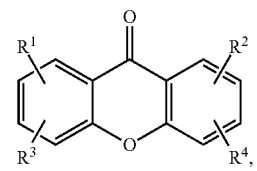

(1)

where each of $R^1$, $R^2$, $R^3$, and $R^4$ is independently a hydrogen atom, a hydroxyl group, a halogen atom, or a C1 to C8 organic group which may contain one or more atoms selected from the group consisting of a hydrogen atom, a nitrogen atom, an oxygen atom, a sulfur atom, and a halogen atom. This allows various substances to be examined as a test substance, and enables a highly accurate and easy measurement of a binding affinity between the test substance and a nucleic acid.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

Industrial Applicability

A composition of the present invention enables a highly accurate and easy screening for drugs (e.g., medicines, agricultural chemicals) targeting nucleic acids. Therefore, a composition of the present invention can be utilized in the pharmaceutical industry, for example.

The invention claimed is:

1. A method for measuring a binding affinity between an RNA and a test substance, comprising:

a first measuring step for measuring fluorescence emitted in response to irradiation of light onto a first solution obtained by (i) mixing the RNA with an organic fluorescent substance which emits fluorescence having an intensity greater while the organic fluorescent substance is liberated from the RNA than while the organic fluorescent substance is bound to the RNA, and (ii) binding the organic fluorescent substance to the RNA;

a second measuring step for measuring fluorescence emitted in response to irradiation of light onto a second solution obtained by further mixing the first solution with the test substance, and if the binding affinity between the test substance and the RNA is higher than the binding affinity between the organic fluorescent substance and the RNA, the organic fluorescent substance bound to the RNA is substituted with the test substance thereby liberating the organic fluorescent substance from the RNA, wherein the liberated organic fluorescent substance emits fluorescence in the second solution; and a comparing step for comparing (i) the fluorescence measured in the first measuring step with (ii) the fluorescence measured in the second measuring step, and calculating an amount of increase in intensity of fluorescence emitted from the second solution with respect to an intensity of fluorescence emitted from the first solution, wherein the organic fluorescent substance is a compound represented by the following General Formula (1):

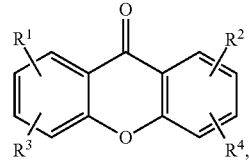

where each of $R^1$, $R^2$, $R^3$, and $R^4$ is independently a hydrogen atom, a hydroxyl group, a halogen atom, or a C1 to C8 containing group selected from the group consisting of —O—$(CH_2)_n$—$NH_2$ where n is 2, 3, 4 or 5, —O—$(CH_2)_n$—$CH(R_{10})NH_2$ where n is 1 or 2 and $R_{10}$ is an alkyl group or a carboxyl group, and an alkyl group, and wherein the RNA is (1) an RNA formed by hybridization of an RNA having a base sequence shown in SEQ ID NO: 1 with an RNA having a base sequence shown in SEQ ID NO: 2, (2) an RNA formed by hybridization of an RNA having a base sequence shown in SEQ ID NO: 1 with an RNA having a base sequence shown in SEQ ID NO: 3, or (3) an RNA having a base sequence shown in SEQ ID NO: 8.

2. The method as set forth in claim 1, wherein the compound is represented by the following General Formula (2):

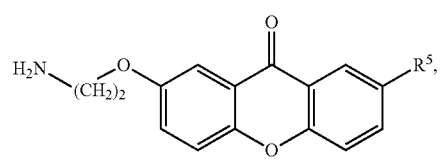

where $R^5$ is a hydrogen atom, a hydroxyl group, a halogen atom, or a C2 to C8 containing group selected from the group consisting of —O—$(CH_2)_n$—$NH_2$ where n is 2, 3, 4 or 5, —O—$(CH_2)_n$—$CH(R_{10})NH_2$ where n is 1 or 2 and $R_{10}$ is an alkyl group or a carboxyl group, and an alkyl group.

3. The method as set forth in claim 1, wherein the compound is represented by the following Structural Formula (3):

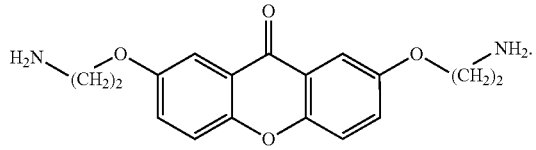

(3)

4. The method as set forth in claim 1, wherein the compound is represented by the following General Formula (12):

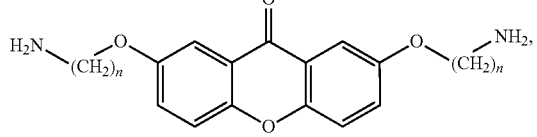

(12)

where n is 3, 4, or 5.

5. The method as set forth in claim 1, wherein the compound is represented by the following Structural Formula (13):

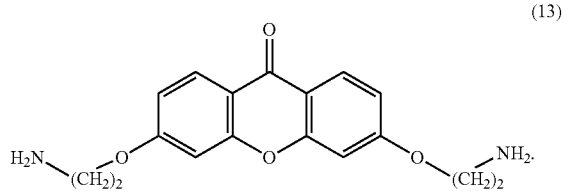

(13)

6. The method as set forth in claim 1, wherein the compound is represented by the following General Formula (14):

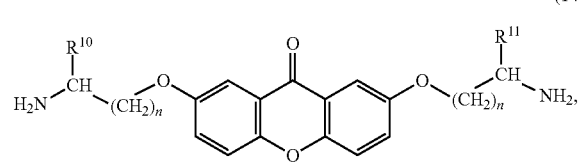

(14)

where n is 1 or 2; and each of $R^{10}$ and $R^{11}$ is independently an alkyl group or a carboxyl group.

* * * * *

SEQUENCE LISTING

```
<160> NUMBER OF SEQ ID NOS: 8

<210> SEQ ID NO 1
<211> LENGTH: 11
<212> TYPE: RNA
<213> ORGANISM: Artificial Sequence
<220> FEATURE:
<223> OTHER INFORMATION: Description of Artificial Sequence:Artificially
      Synthesized Sequence

<400> SEQUENCE: 1
cuaacuaaau g                                                            11

<210> SEQ ID NO 2
<211> LENGTH: 12
<212> TYPE: RNA
<213> ORGANISM: Artificial Sequence
<220> FEATURE:
<223> OTHER INFORMATION: Description of Artificial Sequence:Artificially
      Synthesized Sequence
<220> FEATURE:
<221> NAME/KEY: misc_feature
<222> LOCATION: (6)..(6)
<223> OTHER INFORMATION: n stands for any base

<400> SEQUENCE: 2
cauuunaguu ag                                                           12

<210> SEQ ID NO 3
<211> LENGTH: 11
<212> TYPE: RNA
<213> ORGANISM: Artificial Sequence
<220> FEATURE:
<223> OTHER INFORMATION: Description of Artificial Sequence:Artificially
      Synthesized Sequence

<400> SEQUENCE: 3
cauuuaguua g                                                            11

<210> SEQ ID NO 4
<211> LENGTH: 35
<212> TYPE: RNA
<213> ORGANISM: Human immunodeficiency virus type 1

<400> SEQUENCE: 4
ggucugggcg cagcgcaagc ugacgguaca aggcc                                  35

<210> SEQ ID NO 5
<211> LENGTH: 22
<212> TYPE: PRT
<213> ORGANISM: Human immunodeficiency virus type 1

<400> SEQUENCE: 5

Thr Arg Gln Ala Arg Arg Asn Arg Arg Arg Trp Arg Glu Arg Gln
1               5                   10                  15
```

```
Arg Ala Ala Ala Ala Arg
            20

<210> SEQ ID NO 6
<211> LENGTH: 12
<212> TYPE: PRT
<213> ORGANISM: Homo sapiens

<400> SEQUENCE: 6

Thr Trp Thr Ala Asn Val Gly Lys Gly Gln Pro Ser
1               5                   10

<210> SEQ ID NO 7
<211> LENGTH: 12
<212> TYPE: RNA
<213> ORGANISM: Artificial Sequence
<220> FEATURE:
<223> OTHER INFORMATION: Description of Artificial Sequence:Artificially
      Synthesized Sequence

<400> SEQUENCE: 7
cauuuuaguu ag                                                        12

<210> SEQ ID NO 8
<211> LENGTH: 34
<212> TYPE: RNA
<213> ORGANISM: Human immunodeficiency virus type 1

<400> SEQUENCE: 8
ggucugggcg cagcgcaagc ugacgguaca ggcc                                34
```